US010058520B2

(12) United States Patent
Song et al.

(10) Patent No.: US 10,058,520 B2
(45) Date of Patent: Aug. 28, 2018

(54) COMPOSITIONS AND METHODS FOR TREATING ALZHEIMER'S DISEASE AND DEMENTIA

(75) Inventors: Moon K. Song, Los Angeles, CA (US); James John Schultz, Los Angeles, CA (US); Stephen A. O'Barr, Los Angeles, CA (US)

(73) Assignee: Department of Veterans Affairs, Washington, DC (US)

( * ) Notice: Subject to any disclaimer, the term of this patent is extended or adjusted under 35 U.S.C. 154(b) by 1430 days.

(21) Appl. No.: 12/040,610

(22) Filed: Feb. 29, 2008

(65) Prior Publication Data
US 2009/0004291 A1 Jan. 1, 2009

Related U.S. Application Data

(60) Provisional application No. 60/892,785, filed on Mar. 2, 2007.

(51) Int. Cl.
| | | |
|---|---|---|
| A61K 33/32 | (2006.01) | |
| A61K 31/50 | (2006.01) | |
| A61K 31/415 | (2006.01) | |
| A61K 31/198 | (2006.01) | |
| A61K 33/30 | (2006.01) | |
| A61K 38/05 | (2006.01) | |
| A61K 45/06 | (2006.01) | |

(52) U.S. Cl.
CPC ............ *A61K 31/198* (2013.01); *A61K 33/30* (2013.01); *A61K 38/05* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,411,748 A | 5/1995 | Song | |
| 5,834,032 A | 11/1998 | Song | |
| 5,997,908 A | 12/1999 | Song | |
| 6,090,780 A | 7/2000 | Prasad | |
| 6,821,745 B2 | 11/2004 | Smith | |
| 7,144,865 B2 | 12/2006 | Song | |
| 7,202,279 B1 * | 4/2007 | Kozikowski et al. | ........ 514/659 |
| 8,039,431 B2 | 10/2011 | Wilson et al. | |
| 8,202,992 B2 | 6/2012 | Stevenson et al. | |
| 8,424,518 B2 | 4/2013 | Smutney et al. | |

OTHER PUBLICATIONS

Stuerenburg et al. Free Thyroxine, Cognitive Decline, and Depression in Alzheimer's Disease. Neuro Endocrinol Lett 27(4), 535-537 (2006).*
Kalmijn et al. Subclinical hyperthyroidism and the risk of dementia. The Rotterdam study. Clinical Endocrinology 53, 733-737 (2000).*
Haan, M.N. Therapy insight: type 2 diabetes mellitus and the risk of late-onset Alzheimer's disease. Nature Clinical Practice Neurology, 2 (3), pp. 159-166 (Mar. 2006).*
O'Barr et al. Thyroid Hormone Regulates Endogenous Amyloid-b Precursor Protein Gene Expression and Processing in Both In Vitro and In Vivo Models. Thyroid 16 (12), pp. 1207-1213 (2006).*
Kurochkin, I.V. Insulin-degrading enzyme: embarking on amyloid destruction. Trends Biochem Sci. 26(7) pp. 421-425 (2001).*
Song et al. Insulysin: An Allosteric Enzyme As a Target for Alzheimer's Disease. J. Mol. Neurosci. vol. 25, pp. 201-205 (2005).*
Pittman, et al., *Abnormalities of Thyroid Hormone Turnover in Patients with Diabetes Mellitus Before and After Insulin Therapy*, Journal of Clinical Endocrinology and Metabolism, 1979, vol. 48, No. 5, p. 854-860.
Chomczynski, et al., *Single-Step Method of RNA Isolation by Acid Guanidinium*, Analytical Biochemistry, 1987, p. 156-159.
Evans, et al., *Prevalence of Alzheimer's Disease in a Community Population of Older Person. Higher than Previously Reported*, JAMA, Nov. 10, 1989, vol. 262, No. 18, p. 2551-2556.
Percy, et al., *Autoimmune Thyroiditis Associated with Mild "Subclinical" Hypothyroidism in Adults with Down Syndrome: A Comparison of Patients with and without Manifestations of Alzheimer Disease*, 1990, American Journal of Medical Genetics, p. 148-154.
Martins, et al., *The Molecular Pathology of Amyloid Deposition in Alzheimer's Disease*, Molecular Neurobiology, 1991, vol. 5, p. 389-398.
Pahlsson, et al., *N-Linked Glycosylation β-Amyloid Precursor Protein*, Biochemical and Biophysical Research Communications, Dec. 30, 1992, vol. 189, No. 3, p. 1667-1673.
Zgombic, et al., *DNA Elements Mediating Retinoid and Thyroid Hormone Regulation of Alcohol Dehydrogenase Gene Expression*, Enzymology and Molecular Biology of Carbonyl Metabolism 4, 1993, p. 571-580.
Chin, et al., *Thyroid Hormone Regulation of Thyrotropin Gene Expression*, Recent Progress in Hormone Research, 1993, vol. 48, p. 393-414.
Monzani, et al., *Subclinical Hypothyroidism: Neurobehavioral Features and Beneficial Effect of L-Thyroxine Treatment*, The Clinical Investigator, May 1993, vol. 71, No. 5, p. 367-371.
Tanzi, et al., *Genetic Heterogeneity of Gene Defects Responsible for Familial Alzheimer Disease*, Genetica, 1993, p. 255-263.
Sorbi, et al., *Molecular Genetics of Alzheimer's Disease in Italian Families*, Neurochem, Int., 1994, vol. 25, No. 1, p. 81-84.

(Continued)

*Primary Examiner* — Jeffrey S Lundgren
*Assistant Examiner* — Michael J Schmitt
(74) *Attorney, Agent, or Firm* — Maier & Maier, PLLC

(57) ABSTRACT

The present invention relates to a method of treating, preventing, or delaying the onset of Alzheimer's disease and/or dementia in mammals. More particularly, the invention relates to method of administration of compositions containing defined chemical species useful for treating, preventing, or delaying the onset of Alzheimer's disease and/or dementia in mammals. In some embodiments, a composition used in connection with such methods comprises one or more of 1) thyroid hormone and 2) cyclo(His-Pro) and a zinc salt. Such compositions may also be used to treat metabolic syndrome and cerebrovascular diseases.

34 Claims, 8 Drawing Sheets

(56) References Cited

OTHER PUBLICATIONS

Webster, et al., *Enhanced Aggregation and β Structure of Amyloid β Peptide After Coincubation With C1Q*, Journal of Neuroscience Research, 1994, p. 448-456.
Ernst, et al., *The US Economic and Social Costs of Alzheimer's Disease Revisited*, American Journal of Public Health, Aug. 1994, vol. 84, No. 8, p. 1261-1264.
Chao, et al., *Serum Cytokine Levels in Patients with Alzheimer's Diesease, Clinical and Diagnostic Laboratory Immunology*, vol. 1, No. 4, Jul. 1994, p. 433-436.
Flanders, et al., *Altered Expression of Transforming Growth Factor-β in Alzheimer's Disease*, Neurology, Aug. 1995, 45, p. 1561-1569.
Ganguli, et al., *Association Between Dementia and Elevated TSH: A Community-Based Study, Society of Biological Psychiatry*, 1996, p. 714-725.
Sandbrink, et al., *APP Gene Family Alternative splicing Generates Functionally Related Isoforms*, Annals New York Academy of Sciences, 1996, p. 281-287.
O'Barr, et al., *Expression of the Protooncogene bcl-2 in Alzheimer's Disease Brain, Neurobiology of Aging*, 1996, vol. 17, No. 1 p. 131-136.
Song, et al., *Animal Prostate Extract Ameliorates Diabetic Symptoms by Stimulating Intestinal Zinc Absorption in Rats*, Diabetes Research, 1996, p. 157-170.
Belandia, et al., *Thyroid Hormone Negatively Regulates the Transcriptional Activity of the β-Amyloid Precursor Protein Gene*, The Journal of Biological Chemistry, Nov. 13, 1998, vol. 273, No. 46, p. 30366-30371.
Yamada, et al., *Abundance of Cyclo (HIS-PRO)-Like Immunoreactivity in the Brain of TRH-Deficient Mice*, The Endocrine Society, 1999, vol. 140, No. 1, p. 538-541.
Qi, et al., *Regulation of the mdm2 Oncogene by Thyroid Hormone Receptor*, Molecular and Cellular Biology, Jan. 1999, vol. 19, No. 1, p. 864-872.
Cooper, et al., *Focal Inflammation in the Brain; Role in Alzheimer's Disease*, Immunologic Research, 2000, p. 159-165.
Yu, et al., *MDM2-Dependent Ubiquitination of Nuclear and Cytoplasmic P53*, Onogene, 2000, p. 5892-5897.
O'Barr, et al., *The C5a Complement Activation Peptide Increases IL-1β and IL-6 Release from Amyloid-β Primed Human Momocytes: Implications for Alzheimer's Disease*, Journal of Neuroimmunology, 2000, p. 87-94.
Canaris, et al., *The Colorado Thyroid Disease Prevalence Study*, Arch Intern Med., Feb. 28, 2000, vol. 160, p. 526-534.
Perez-Juste, et al., *An Element in the Region Responsible for Premature Termination of Transcription Mediates Repression of c-myc Gene Expression by Thyroid Hormone in Neuroblastoma Cells*, The Journal of Biological Chemistry, Jan. 14, 2000, vol. 275, No. 2, p. 1307-1314.
Kogai, et al., *Retinoic Acid Induces Sodium/Iodide Symporter Gene Expression and Radioiodide Uptake in the MCF-7 Breast Cancer Cell Line*, PNAS, Jul. 18, 2000, vol. 97, No. 15, p. 8519-8524.
Gouveia, et al., *Thyroid Hormone Stimulation of Osteocalcin Gene Expression in ROS 17/2.8 Cells is Mediated by Transcriptional and Post-Transcriptional Mechanisms*, Journal of Endocrinology, 2001, 170, p. 667-675.
O'Barr, et al., *Neuronal Expression of a Functional Receptor for the C5a Complement Activation Fragment*, The American Association of Immunologists, 2001, p. 4154-4162.
Rosenthal, et al., *Effects of Arachidonic Acid and Cyclo (His-Pro) on Zinc Transport Across Small Intestine and Muscle Tissues*, Life Science, 2001, p. 337-348.
Kulnane, et al., *Neuropathological Characterization of Mutant Amyloid Precursor Protein Yeast Artificial Chromosome Transgenic Mice*, Neurobiology of Disease, 2001, p. 982-992.

Ribeiro, et al., *Thyroid Hormone-Sympathetic Interaction and Adaptive Thermogenesis are Thyroid Hormone Receptor Isoform-Specific*, The Journal of Clinical Investigation, Jul. 2001, vol. 108, No. 1, p. 97-105.
Gouveia, et al., *Thyroid Hormone Gene Targets in ROS 17/2.8 Osteoblast-Like Cells Identified by Differential Display Analysis*, Thyroid, 2002, vol. 12, No. 8, p. 663-671.
Hwang, et al., *Effects of Arachidonic Acid Plus Zinc on Glucose Disposal in Genetically Diabetic (ob/ob) Mice*, Diabetes, Obesity and Metabolism, 2002, p. 124-131.
Hwang, et al., *Effects of Cyclo (his-pro) Plus Zinc on Glucose Metabolism in Genetically Diabetic Obese Mice*, Diabetes, Obesity and Metabolism, 2003, p. 317-324.
Nygard, et al., *Hormone-Dependent Repression of the E2F-1 Gene by Thyroid Hormone Receptors*, Molecular Endocrinology, 2003, 17(1), p. 79-92.
Pastor, et al., *Apolipoprotein EE4 Modifies Alzheimer's Disease Onset in an E280A PS1 Kindred*, American Neurological Association, 2003, p. 163-169.
Song, et al., *Anti-Hyperglycemic Activity of zinc Plus Cyclo (His-Pro) in Genetically Diabetic Goto-Kakizaki and Aged Rats*, Society for Experimental Biology and Medicine, 2003, p. 1338-1345.
Davis, et al., *Cognitive and Neuropsychiatric Aspects of Subclinical Hypothyroidism: Significance in the Elderly*, Current Psychiatry Reports, 2003, p. 384-390.
Song, et al., *Antidiabetic Actions of Arachidonic Acid and Zinc in Genetically Diabetic Goto-Kakizaki Rats*, Metabolism, Jan. 2003, vol. 52, No. 1, p. 7-12.
Cook, et al., *Reduced Hippocampal Insulin-Degrading Enzyme in Late-Onset Alzheimer's Disease is Associated with the Apolipoprotein E-E4 Allele*, American Journal of Pathlology vol. 162, No. 1, Jan. 2003, p. 313-319.
Farris, et al., *Insulin-Degrading Enzyme Regulates the Levels of Insulin, Amyloid β-Protein, and the β-Amyloid Precursor Protein Intracellular Domain in Vivo*, PNAS, vol. 100, No. 7, Apr. 7, 2003, p. 4162.4167.
Lesne, et al., *Transforming Growth Factor-β1 Poteneiates Amyloid-β Generation in Astrocytes and in Transgenic Mice*, The Journal of Biological Chemistry, May 2003, vol. 278, No. 20, p. 18408-18418.
Miller, et al., *Amyloid-β Peptide Levels in Brain are Inversely Correlated with Insulysin Activity Levels In Vivo*, PNAS, May 13, 2003, vol. 100, No. 10, p. 6221-6226.
Kawai, et al., *Critical Contribution of the MDM2 Acidic Domain to p53 Ubiquitination, Molecular and Cellular Biology*, Jul. 2003, vol. 23, No. 14, p. 4939-4947.
Hebert, et al., *Alzheimer Disease in the US Population*, Arch Neurol, American Medical Association, Aug. 2003, vol. 60, p. 1119-1122.
Lehman, et al., *Alterations in β-Amyloid Production and Deposition in Brain Regions of Two Transgenic Models*, Neurobiology of Aging, 2004, p. 645-653.
Gong, et al., *Alzheimer's Disease-Affected Brain: Presence of Oligomeric Aβ Ligands (ADDLs) Suggests a Molecular Basis for Reversible Memory Loss*, PNAS, Sep. 2, 2003, vol. 100, No. 18 p. 10417-10422.
Liu, et al., *A Thyroid Hormone Receptor a Gene Mutation (P398H) is Associated with Visceral Adiposity and Impaired Catecholamine-Stimulated Lipolysis in Mice*, The Journal of Biological Chemistry, Oct. 3, 2003, vol. 278, No. 40, p. 38913-38920.
Sanchez-Pacheco, et al., *Binding of the Thyroid Hormone Receptor to a Negative Element in the Basal Growth Hormone Promoter is Associated with Histone Acetylation*, The Journal of Biological Chemistry, Oct. 10, 2003, vol. 278, No. 41, p. 39383-39391.
Song, et al., *Substrate Activation of Insulin-Degrading Enzyme (Insulysin)*, The Journal of Biological Chemistry, Dec. 12, 2003, vol. 278, No. 50, p. 49789-49794.
Leissring, et al., *Enhanced Proteolysis of β-Amyloid in APP Report Transgenic Mice Prevents Plaque Formation, Secondary Pathology, and Premature Death*, Neuron, Dec. 18, 2003, vol. 40, p. 1087-1093.

(56) References Cited

OTHER PUBLICATIONS

Kim, et al., *A Novel Cell Type-Specific Mechanism for Thyroid Hormone-Dependent Negative Regulation of the Human Type 1 Deiodinase Gene*, Molecular Endocrinology, 2004, 18 (12):924-2936.
Shen, et al., *Thyroid Hormone Regulation of Prohormone Convertase 1 (PC1): Regional Expression in Rat Brain and In Vitro Characterization of Negative Thyroid Hormone Response Elements*, Journal of Molecular Endocirnology, 2004, p. 21-33.
Nicholls, *The Clinical and Biological Relationship Between Type II Diabetes Mellitus and Alzheimer's Disease*, Current Alzheimer Research, 2004, p. 47-54.
Villa, et al., *A Response Unit in the First Exon of the β-Amyloid Precursor Protein Gene Containing Thyroid Hormone Receptor and Sp1 Binding Sites Mediates Negative Regulation by 3,5,3;—Triiodothyronine*, Molecular Endocrinology, 2004, p. 863-873.
Docagne, et al., *Sp1 and Smad Transcription Factors Co-Operate to Mediate TGF-β-Dependent Activation of Amyloid-β Precursor Protein Gene Transcription*, Biochemical Society, 2004, p. 393-399.
Kogai, et al., *Systemic Retinoic Acid Treatment Induces Sodium/Iodide Symporter Expression and Radioiodide Uptake in Mouse Breast Cancer Models*, Cancer Research, Jan. 1, 2004, p. 415-422.
Janson, et al., Increased Risk of Type 2 Diabetes in Alzheimer Disease, Diabetes, Feb. 2004, vol. 53, p. 474-481.
Farris, et al., *Partial Loss-of-Function Mutations in Insulin-Degrading Enzyme that Induce Diabetes also Impair Degradation of Amyloid β-Protein*, American Journal of Pathology, vol. 164, No. 4, Apr. 2004, p. 1425-1434.
Ho et al., *Diet-Induced Insulin Resistance Promotes Amyloidosis in a Transgenic Mouse Model of Alzheimer's Disease*, The FASEB Journal, vol. 18, May 2004, p. 902-904.
Sampaolo, et al., *Increased Cerebrospinal Fluid Levels of 3,3',5'—Triiodothyronine in Patients with Alzheimer's Disease*, The Journal of Clinical Endocrinoloty & Metabolism, 2005, 90(1), p. 198-202.
de la Monte, et al., Review of Insulin and Insulin-Like Growth Factor Expression, Signaling, and Malfunction in the Central Nervous System: Relevance to Alzheimer's Disease, Journal of Alzheimer's Disease, 2005, p. 45-61.
Huang, et al., *Transforming Growth Factor-β Promotes Inactivation of Extracellular Thyroid Hormones via Transcriptional Stimulation of Type 3 Iodothyronine Deiodinase*, Molecular Endocrinology, 2005, 19 (12): 3126-3136.
Shen, et al., *Regulation of Regional Expression in Rat Brain PC2 by Thyroid Hormone/Characterization of Novel Negative Thyroid Hormone Response Elements in the PC2 Promoter*, Am J Physiol Endocrinol Metab, 2005, 288:236-245.
Eckman, et al., *Aβ Degrading Enzymes: Modulators of Alzheimer's Disease Pathogenesis and Targets for Therapeutic Intervention*, Biochemical Society, 2005, vol. 22, Part 5, p. 1101-1105.
Ao, et al., *Altered Glucose and Insulin Responses to Brain Medullary Thyrotropin-Releasing Hormone (TRH)-Induced Autonomic Activation in Type 2 Diabetic Goto-Kakizaki Rats*, The Endocrine Society, 2005, Endocrinology 146(12), p. 5425-5432.

Pollack, et al., *γ-Secretase Inhibitors for Alzheimer's Disease: Challenges of a Promiscuous Protease*, Current Opinion in Investigational Drugs, 2005, vol. 6, No. 1, p. 35-47.
Odetti, et al., *Plasma Levels of Insulin and Amyloid β 42 are Correlated in Patients with Amnestic Mild Cognitive Impairment*, Journal of Alzheimer's Disease 8, 2005, p. 243-245.
Song, et al., *Raw Vegetable Food Containing High Cyclo (His-Pro) Improved Insulin Sensitivity and Body Weight Control*, Metabolism Clinical and Experimental, Science Direct, 2005, 1480-1489.
Song, et al., *Insulysin, An Allosteric Enzyme As a Target for Alzheimer's Disease*, Journal of Molecular Neuroscience, 2005, vol. 25, p. 201-205.
Billings, et al., *Intraneuronal Aβ Causes the Onset of Early Alzheimer's Disease-Related Cognitive Deficits in Transgenic Mice*, Neuron, Mar. 3, 2005, vol. 45, p. 675-688.
Fishel, et al., *Hypetinsulinemia Provokes Synchronous Increases in Central Inflammation and β-Amyloid in Normal Adults*, Arch Neurol, vol. 62, Oct. 2005, p. 1539-1544.
Rosenberg, *Immunotherapy for Alzheimer Disease, The Promise and the Problem*, Arch Neurol., Oct. 2005, vol. 62, p. 1506-1507.
O'Barr, et al., *Thyroid Hormone Regulates Endogenous Amyloid-β Precursor Protein Gene Expression and Processing in Both In Vitro and In Vivo Models*, Thyroid, 2006, vol. 16, No. 12, p. 1207-1213.
Qiu, et al., *Insulin, Insulin-Degrading Enzyme and Amyloid-β Peptide in Alzheimer's Disease: Review and Hypothesis*, Neurobiology of Aging, 2006, vol. 27, p. 190-198.
Laurberg, et al., *Hypothyroidism in the Elderly: Pathophysiology*, Diagnosis and Treatment, Drugs Aging, 2006, p. 23-38.
A. Faden, et al., *Novel Small Peptides with Neuroprotective and Nootropic Properties*, Journal of Alzheimer's Disease 6 (2004), pp. 593-597.
International Search Report and Written Opinion, International Application No. PCT/US08/55508, dated Aug. 5, 2008, in 9 pages.
Gironi M, Borgiani B, Fariana E. et al. A global immune deficit in Alzheimer' disease and mild cognitive impairment disclosed by a novel data mining process. J. Alzheimers Dis. 43:1199-1213, 2015.
Blacher E, Dadali T, Bespalko A. et. al. Alzheimer's disease pathology is attenuated in a CD38-deficient mouse model.
Cherry JD, Olschowka JA, O'Bannon MK. Arginase 1+ microglia reduce AB plaque deposition during iL-1B-dependent neuroinflammation . J Neuroinflammation 12:203 p. 1-13, 2015.
Hagenaars, M. et al. The development of a bi-specific anti-CD161A x anti-tumor antibody for rat NK cell targeting. Immunobiology 1999, 200(1):31-48.
Jin, Jing, et al. CD11b-CD27-NK Cells are Associated with the Progression of Lung Carcinoma. PLoS One 2013, 8 (4): e61024.
Ilett, E.J. et al. The evolving role of dendritic cells in cancer therapy. Expert Opin Bio Ther. Mar. 2010; 10(3):369-79.
Maynard et al., "Metals and amyloid-β in Alzheimer's disease", Int. J. Exp. Path. (2005), 86, 147-159.
A. Minelli et al., Focus on cyclo(His-Pro): History and perspectives as antioxidant peptide. Amino Acids 2008 35 (2):283-9; 7 pages.

\* cited by examiner

Aβ 1-42 and 1-40 in Hyperthyroid and Hypothyroid Mouse Brain (p ≤ -0.05)

COMPOSITIONS AND METHODS FOR TREATING ALZHEIMER'S DISEASE AND DEMENTIA

RELATED APPLICATIONS

This application claims the priority benefit under 35 U.S.C. § 119(e) of the U.S. provisional applications 60/892,785, filed Mar. 2, 2007, which is hereby incorporated by reference in its entirety.

BACKGROUND

Field of the Invention

The present invention relates to methods for treating or preventing Alzheimer's disease and/or dementia. More particularly, the invention relates to methods of administration of compositions containing defined chemical species useful for prevention and treatment of Alzheimer's disease and/or dementia.

Description of the Related Art

Amyloid beta (Aβ) protein is the main constituent of amyloid plaques in the brains of Alzheimer's disease ("AD") patients. Similar plaques appear in some variants of Lewy body dementia and in inclusion body myositis, a muscle disease. Aβ also forms aggregates coating cerebral blood vessels in cerebral amyloid angiopathy.

Aβ is formed after sequential cleavage of the amyloid precursor protein (APP) by the β- and γ-secretases. APP is an integral membrane protein synthesized from transcripts derived by alternative splicing of RNA transcribed from a single gene. Following translation, each APP may be processed by either alpha secretase or beta plus gamma secretase cleavage pathways to yield the mature glycosylated protein plus the carboxyterminal cleavage products. All three major transcripts and one minor transcript, termed APP-695, -751, -770, and -714, encode the Aβ sequence. This peptide is the major component of the plaques observed in AD. Alpha secretase cleavage occurs within the Aβ containing region of APP, precluding Aβ formation. Beta and subsequent gamma cleavage of APP results in the formation of the Aβ peptide and a membrane component smaller than that derived from alpha secretase cleavage.

Autosomal-dominant mutations in APP cause hereditary early-onset Alzheimer's disease, likely as a result of altered proteolytic processing. Increases in either total Aβ levels or the relative concentration of both $A\beta_{40}$ and $A\beta_{42}$ (where the former is more concentrated in cerebrovascular plaques and the latter in neuritic plaques) have been implicated in the pathogenesis of both familial and sporadic Alzheimer's disease. Due its more hydrophobic nature, the $A\beta_{42}$ is the most amyloidogenic form of the peptide. The "amyloid hypothesis", that the plaques are responsible for the pathology of Alzheimer's disease, is accepted by the majority of researchers but is by no means conclusively established.

Although several kindred with mutations in the APP gene and apoE genes have been identified and present with AD, the majority of AD cases are age-related and occur without defined cause. It is estimated that over 10% of those over the age of 65 will develop Alzheimer's disease. An estimated 4.5 million Americans have AD, and national costs of caring for them are at least $100 billion.

SUMMARY OF THE INVENTION

Embodiments of the invention broadly relate to the prevention or treatment of dementia in mammals by the administration of certain defined chemical species. Certain embodiments relate to the treatment or prevention of Alzheimer's Disease which is one of the most common causes of dementia in mammals. However, the invention may be used to treat or prevent other forms of dementia such as vascular dementia. Embodiments also relate to delaying the onset of symptoms of Alzheimer's Disease and dementia.

In one embodiment, a method of treating, preventing or delaying the onset of symptoms of Alzheimer's Disease or dementia includes administering a pharmaceutically effective amount of zinc salt and a pharmaceutically effective amount of cyclo-His-Pro. In certain embodiments, the zinc salt and the cyclo-His-Pro are administered in the same composition. In other embodiments, the zinc salt and the cyclo-His-Pro are administered in different compositions.

In the above embodiment, the zinc salt and the cyclo-His-Pro may be administered in varying amounts. In some embodiments, the weight ratio of zinc to cyclo-Hispro is from about 1:100 to about 100:1. In some embodiments, the weight ratio of zinc to cyclo-Hispro is from about 1:10 to about 100:1. In some embodiments, the weight ratio of zinc to cyclo-Hispro is from about 1:6 to about 5:1. In some embodiments, the weight ratio of zinc to cyclo-Hispro is from about 1:15 to about 20:1. In some embodiments, the weight ratio of zinc to cyclo-Hispro is from about 1:30 to about 4:1. In some embodiments, the weight ratio of zinc to cyclo-Hispro is from about 1:8 to about 4:1. In some embodiments, the weight ratio of zinc to cyclo-Hispro is from about 1:40 to about 40:1. Zinc as noted above relates to the amount of zinc cation.

In certain embodiments, the zinc salt and cyclo-Hispro are administered in an amount that causes an increased serum level of insulin degrading enzyme in the mammal. In certain embodiments, the serum level is increased in an amount ranging between 0.001% to about 0.5%. In certain embodiments, the serum level is increased in an amount ranging between 0.01% to about 1%. In certain embodiments, the serum level is increased in an amount ranging between 0.1% to about 5%. In certain embodiments, the serum level is increased in an amount ranging between 1% to about 10%. In certain embodiments, the serum level is increased in an amount ranging between 1% to about 50%.

In certain embodiments, the zinc salt and cyclo-Hispro are administered to the mammal in an amount that causes a decrease in a serum level of amyloid beta protein In certain embodiments, the serum level is decreased in an amount ranging between 0.001% to about 0.5%. In certain embodiments, the serum level is decreased in an amount ranging between 0.01% to about 1%. In certain embodiments, the serum level is decreased in an amount ranging between 0.1% to about 5%. In certain embodiments, the serum level is decreased in an amount ranging between 1% to about 10%. In certain embodiments, the serum level is decreased in an amount ranging between 1% to about 50%.

In certain embodiments, the zinc cation of the zinc salt is administered to the mammal in an amount from about 0.01 to about 4 mg/kg/day. In one embodiment, a zinc cation of the zinc salt is administered mammal in an amount from about 0.01 to about 1.5 mg/kg/day. In another embodiment, a zinc cation of the zinc salt is administered to the mammal in an amount from about 0.01 to about 0.4 mg/kg/day. In another embodiment, a zinc cation of the zinc salt is administered to the mammal in an amount from about 0.1 to about 2 mg/kg/day. In another embodiment, a zinc cation of the zinc salt is administered to the mammal in an amount from about 2 to about 4 mg/kg/day. In another embodiment, a zinc cation of the zinc salt is administered to the mammal in an amount from about 1 to about 10 mg/kg/day. In another embodiment, a zinc cation of the zinc salt is administered to the mammal in an amount from about 3 to about 8 mg/kg/day. In another embodiment, a zinc cation of the zinc salt is administered to the mammal in an amount from about 4 to about 7 mg/kg/day. In another embodiment, a zinc cation of the zinc salt is administered to the mammal in an amount from about 7 to about 10 mg/kg/day. In another embodiment, a zinc cation of the zinc salt is administered to the mammal in an amount from about 0.01 to about 0.1.8 mg/kg/day. In another embodiment, a zinc cation of the zinc salt is administered to the mammal in an amount from about 1 to about 1.5 mg/kg/day.

In any of the above mentioned embodiments, cyclo-Hispro may be administered to the mammal in an amount from about 0.007 to about 1.4 mg/kg/day. In some embodiments, cyclo-Hispro is administered to the mammal in an amount from about 0.01 to about 5 mg/kg/day. In some embodiments, cyclo-Hispro is administered to the mammal in an amount from about 0.01 to about 2 mg/kg/day. In some embodiments, cyclo-Hispro is administered to the mammal in an amount from about 2 to about 7 mg/kg/day. In some embodiments, cyclo-Hispro is administered to the mammal in an amount from about 3 to about 5 mg/kg/day. In some embodiments, cyclo-Hispro is administered to the mammal in an amount from about 7 to about 10 mg/kg/day. In some embodiments, cyclo-Hispro is administered to the mammal in an amount from about 0.5 to about 2 mg/kg/day. In some embodiments, cyclo-Hispro is administered to the mammal in an amount from about 0.2 to about 4 mg/kg/day. In some embodiments, cyclo-Hispro is administered to the mammal in an amount from about 0.8 to about 3 mg/kg/day. In some embodiments, cyclo-Hispro is administered to the mammal in an amount from about 1 to about 6 mg/kg/day.

In any of the above mentioned embodiments, thyroid hormone or thyroxine, a form of thyroid hormone, may also be administered to treat, prevent or delay the onset of symptoms of Alzheimer's Disease. In certain embodiments, L-thyroxine is administered to the mammal in an amount from about 0.1 to about 15 µg/kg/day. In certain embodiments, L-thyroxine is administered to the mammal in an amount from about 0.001 to about 0.010 µg/kg/day. In certain embodiments, L-thyroxine is administered to the mammal in an amount from about 0.001 to about 0.1 µg/kg/day. In certain embodiments, L-thyroxine is administered to the mammal in an amount from about 0.05 to about 1 µg/kg/day. In certain embodiments, L-thyroxine is administered to the mammal in an amount from about 0.03 to about 0.2 µg/kg/day. In certain embodiments, L-thyroxine is administered to the mammal in an amount from about 0.04 to about 4 µg/kg/day. In certain embodiments, L-thyroxine is administered to the mammal in an amount from about 0.08 to about 0.5 µg/kg/day. In certain embodiments, L-thyroxine is administered to the mammal in an amount from about 0.001 to about 30 µg/kg/day.

In certain embodiments, L-thryroxine may be administered without zinc salt or cyclo-Hispro to treat, prevent or reduce the onset of symptoms of Alzheimer's disease. In these embodiments, L-thyroxine may be administered in a pharmaceutically effective amount. In some embodiments, the amount causes a reduction in a serum level of amyloid-beta plaques. In some embodiment, the amount that is administered causes an increase in a serum level of thyroxine in the mammal. In some embodiment, the increase in serum level is between about 2 to about 300% greater than the original thyroxine serum level in the mammal. In some embodiment, the increase in serum level is between about 50 to about 250% greater than the original thyroxine serum level in the mammal. L-thyroxine can be administered without zinc and cyclo-Hispro in any of the amount mentioned above in relation to the other embodiments.

In certain embodiments, other derivatives of thyroid hormone may be administered with or without zinc and cyclo-Hispro. In some embodiments, L-triiodothyronine may be administered to mammal in a pharmaceutically effective amount to treat, prevent, or delay the onset of symptoms of Alzheimer's disease or dementia.

DETAILED DESCRIPTION OF THE PREFERRED EMBODIMENT

Figure 1:
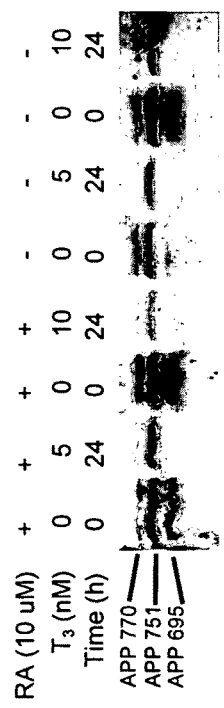
FIG. 1 is a western blot illustrating the effect of T3 on human neuroblastoma cells.

Alzheimer's disease (AD) neuropathology is characterized by amyloid-beta (Aβ) containing plaques and neurofibrillary tangles composed of neurofilament and hyperphosphorylated tau protein. Aβ has been demonstrated to be neurotoxic in numerous studies, and appears to be responsible for initiating the memory loss associated with AD. Without wishing to be bound to any particular theory, decreasing Aβ plaque load would presumably reduce the pathology and cognitive difficulties associated with this disease. Aβ levels can be controlled by one or more methods, including, but not limited to, regulating amyloid precursor protein (APP) gene expression, regulating APP processing to form Aβ, and controlling or causing Aβ degradation.

Certain aspects of embodiments relate to the use of pharmaceutical compositions in the treatment, prevention, or delay of onset of AD and/or dementia in mammals. In one embodiment, pharmaceutical compositions comprise one or more of: (1) thyroid hormone or (2) a zinc salt and cyclo-Hispro (CHP). Such compositions may also be used to treat, prevent, or delay the onset of metabolic disease. These compositions and methods of administering the same are further described herein.

While the inventors do not ascribe to any one single theory, it is believe that treatments of mammals with thyroid hormone results in down-regulating APP gene expression via a putative negative response element in the APP gene. Furthermore, it is believe that zinc and CHP cause increased activation of insulin-degrading enzyme (IDE) which causes increased Aβ degradation. Such therapies may be used alone or as a combination therapy for the treatment of AD or dementia. Thus, two biologically safe treatment strategies, which reduce formation of Aβ, enhance endogenous metabolism of Aβ in vivo, and/or improve spatial memory, have been developed.

In some embodiments, these ingredients of the pharmaceutical compositions can be included in "purified" form. By the use of the term "purified", it is intended to mean that these ingredients are in a form enriched relative to the form in which they can be obtained from nature, such as in a prostate extract. The purified ingredients can be obtained either by enriching from a natural source thereof, or by a chemically synthetic method. Thus, the use of the term "purified" does not necessarily imply that these ingredients are completely free, or even substantially free, of other components. Nevertheless, a "purified" ingredient is enriched relative to its concentration in a natural state.

The method of administering a composition of a thyroid hormone, zinc salt, and/or CHP may be accomplished by any means. In some embodiments, it is accomplished by ingestion of a tablet, hard or soft capsules, powder, pill, drink, or lozenges. The formation of suitable oral dosage forms, may include, but are not limited to, those that are known to those having skill in the art. Compositions intended for oral use may be prepared according to any method, and such compositions may contain one or more agents such as sweetening agents, flavoring agents, coloring agents, and/or preserving agents in order to provide pharmaceutically elegant and palatable preparations. Suitable excipients for tablets and capsules include inert diluents, such as safflower oil, lecithin, inositol, soybean shortening oil, gelatin, acacia, glycerin, titanium oxide and soybean oil. The coating of the capsules can be gelatin or a soluble polymer, as is well understood in the art. The tablets or capsules are suitable for oral administration according to a daily administration regimen.

In addition, the methods may also include administering the composition in single or multiple doses. Some embodiments also include administrating the ingredients of the composition in a stepwise manner, or in a manner in which one or more of the ingredients are mixed and administered prior to the administration of the other ingredients.

One composition useful for treating, preventing or delaying the onset of AD or dementia in a mammal includes thyroid hormone. As described herein, "thyroid hormone" is a broad term and is used in its ordinary sense and includes, without limitation, wherein the context permits, L-thryroxine (T4) and L-triiodothyronine (T3). In one embodiment, each tablet or capsule (or other means of deliver) contains L-thyroxine. L-thyroxine is 3:5,3':5' tetra-iodothyronine (often abbreviated as T4) and is the major hormone secreted by the follicular cells of the thyroid gland. In some embodiments, the thyroxine may be administered in amounts ranging from about 1 to about 300 μg/day. In some embodiments, thyroxine may be administered in amounts ranging from about 1 to about 100 μg/day. In some embodiments, thyroxine may be administered in amounts ranging from about 30 to about 150 μg/day. In some embodiments, thyroxine may be administered in amounts ranging from about 50 to about 100 μg/day. In some embodiments, the thyroxine may be administered in amounts ranging from about 25 to about 50 μg/day. However, the exact dosage form and amount may vary as further described herein. In some embodiments, a thryoxine is administered in a weight dependent fashion. In such case, thyroxine may be administered in amount of about 0.1 to about 3.0 μg/kg/day, including about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, or 2.9 μ/kg/day.

In some embodiments, L-thyroxine is administered to the mammal in an amount from about 0.1 to about 15 μg/kg/day. In certain embodiments, L-thyroxine is administered to the mammal in an amount from about 0.001 to about 0.010 μg/kg/day. In certain embodiments, L-thyroxine is administered to the mammal in an amount from about 0.001 to about 0.1 μg/kg/day. In certain embodiments, L-thyroxine is administered to the mammal in an amount from about 0.05 to about 1 μg/kg/day. In certain embodiments, L-thyroxine is administered to the mammal in an amount from about 0.03 to about 0.2 μg/kg/day. In certain embodiments, L-thyroxine is administered to the mammal in an amount from about 0.04 to about 4 μg/kg/day. In certain embodiments, L-thyroxine is administered to the mammal in an amount from about 0.08 to about 0.5 μg/kg/day. In certain embodiments, L-thyroxine is administered to the mammal in an amount from about 0.001 to about 30 μg/kg/day.

As is recognized by person having ordinary skill in the art, thyroxine (T4) is converted to triiodothyronine (T3), a more active short-acting form of thyroid hormone in the mammal. T3 is derived from T4 by enzymatic conversion in the blood and peripheral tissues. T3 is the more active form of thyroid hormone, and binds to nuclear thyroid hormone receptors in different cells and tissues. In contrast to T4 which has a long half-life of several days, T3 has a short half life (hours), and disappears more rapidly from our blood after a single dose. Hence, T4 treatments allow the body to convert T4 to T3 as needed in a physiologically regulated manner.

In another embodiment, thyroid hormone may be administered as triiodothyronine (T3) to treat AD or dementia in a mammal. In some embodiments, T3 may be administered in amounts ranging from about 0.1 to about 30 μg/day. In some embodiments, T3 may be administered in amounts ranging from about 0.5 to about 20 μg/day. In some embodiments, the T3 may be administered in amounts ranging from about 0.8 to about 10 μg/day. In some embodiments, T3 may be administered in amounts ranging from about 1 to about 5 μg/day. In some embodiments, T3 may be administered in amounts ranging from about 2 to about 7 μg/day. However, the exact dosage form and amount may vary as further described herein. In other embodiments, treatment with a combination of T4 and T3 confers added benefits over the treatment of T4 alone.

In some embodiments, L-triiodothyronine is administered to the mammal in an amount from about 0.1 to about 15

μg/kg/day. In certain embodiments, L-triiodothyronine is administered to the mammal in an amount from about 0.001 to about 0.010 μg/kg/day. In certain embodiments, L-triiodothyronine is administered to the mammal in an amount from about 0.001 to about 0.1 μg/kg/day. In certain embodiments, L-triiodothyronine is administered to the mammal in an amount from about 0.05 to about 1 μg/kg/day. In certain embodiments, L-triiodothyronine is administered to the mammal in an amount from about 0.03 to about 0.2 μg/kg/day. In certain embodiments, L-triiodothyronine is administered to the mammal in an amount from about 0.04 to about 4 μg/kg/day. In certain embodiments, L-triiodothyronine is administered to the mammal in an amount from about 0.08 to about 0.5 μg/kg/day. In certain embodiments, L-triiodothyronine is administered to the mammal in an amount from about 0.001 to about 30 μg/kg/day.

In a further embodiment, a drug that increases the serum levels of thyroid hormone in a mammal may also be used. T4 is naturally produced by the body and enzymatically converted to T3. Thus, one treatment includes administering a drug which increases the serum level of T4 or T3 in the mammal. For example, the administration of iodine may cause an increase in production of T4 in the mammal. Thus, such drugs may be used to increase serum levels of thyroid hormone in the mammal.

Other chemical species useful for treating, preventing or delaying the onset of AD or dementia in a mammal includes zinc and cyclo-Hispro. Earlier works, as disclosed in U.S. Pat. Nos. 5,834,032 and 7,144,865, the disclosures of which are herein incorporated by reference in their entireties, have shown that pharmaceutical compositions comprising zinc and cyclo-HisPro are useful for the treatment of other indications.

As referred to herein, numerical values for zinc represent masses or concentrations of the zinc component of a zinc salt. Examples of zinc salts useful in connection with the invention include zinc chloride and zinc sulfate. Cyclo-Hispro (also referred to herein as "CHP"), a cyclic form of L-histidine and proline, stimulates intestinal zinc transport and cellular zinc uptake. Plasma histidine-proline-rich glycoprotein contains unusual tandems of histidine-proline, and is relatively abundant in plasma. This glycoprotein plays a role in the cellular zinc transport process. Although CHP is a metabolite of thyrotropin releasing hormone (TRH), CHP can be synthesized from different biochemical sources, including histidine-proline-rich glycoprotein. High levels of CHP are present in many food sources, and are readily absorbed in the gut without chemical or enzymatic destruction. CHP intake decreases food intake in rats and humans.

In the above embodiment, the zinc salt and the cyclo-HisPro may be administered in varying amounts. In some embodiments, the weight ratio of zinc to cyclo-Hispro is from about 1:100 to about 100:1. In some embodiments, the weight ratio of zinc to cyclo-Hispro is from about 1:10 to about 100:1. In some embodiments, the weight ratio of zinc to cyclo-Hispro is from about 1:6 to about 5:1. In some embodiments, the weight ratio of zinc to cyclo-Hispro is from about 1:15 to about 20:1. In some embodiments, the weight ratio of zinc to cyclo-Hispro is from about 1:30 to about 4:1. In some embodiments, the weight ratio of zinc to cyclo-Hispro is from about 1:8 to about 4:1. In some embodiments, the weight ratio of zinc to cyclo-Hispro is from about 1:40 to about 40:1. Zinc as noted above relates to the amount of zinc cation.

In one embodiment, a composition may contain an amount of zinc cation ranging from about 1 to about 500 mg, preferably about 10 to about 200 mg, and more preferably about 20 to about 100 mg. In one embodiment, cyclo-Hispro may be present in the same or a different composition in amount ranging from about 0.5 to about 100 mg, with a more preferred range extending from about 10 to about 50 mg. In another embodiment, the amount of cyclo-Hispro present in the administered pharmaceutical composition can range from about 0.5 to about 100 mg, with a more preferred range extending from about 10 to about 70 mg.

In certain embodiments, the zinc cation of the zinc salt is administered to the mammal in an amount from about 0.01 to about 4 mg/kg/day. In one embodiment, a zinc cation of the zinc salt is administered mammal in an amount from about 0.01 to about 1.5 mg/kg/day. In another embodiment, a zinc cation of the zinc salt is administered to the mammal in an amount from about 0.01 to about 0.4 mg/kg/day. In another embodiment, a zinc cation of the zinc salt is administered to the mammal in an amount from about 0.1 to about 2 mg/kg/day. In another embodiment, a zinc cation of the zinc salt is administered to the mammal in an amount from about 2 to about 4 mg/kg/day. In another embodiment, a zinc cation of the zinc salt is administered to the mammal in an amount from about 1 to about 10 mg/kg/day. In another embodiment, a zinc cation of the zinc salt is administered to the mammal in an amount from about 3 to about 8 mg/kg/day. In another embodiment, a zinc cation of the zinc salt is administered to the mammal in an amount from about 4 to about 7 mg/kg/day. In another embodiment, a zinc cation of the zinc salt is administered to the mammal in an amount from about 7 to about 10 mg/kg/day. In another embodiment, a zinc cation of the zinc salt is administered to the mammal in an amount from about 0.01 to about 0.1.8 mg/kg/day. In another embodiment, a zinc cation of the zinc salt is administered to the mammal in an amount from about 1 to about 1.5 mg/kg/day.

In any of the above mentioned embodiments, cyclo-Hispro may be administered to the mammal in an amount from about 0.007 to about 1.4 mg/kg/day. In some embodiments, cyclo-Hispro is administered to the mammal in an amount from about 0.01 to about 5 mg/kg/day. In some embodiments, cyclo-Hispro is administered to the mammal in an amount from about 0.01 to about 2 mg/kg/day. In some embodiments, cyclo-Hispro is administered to the mammal in an amount from about 2 to about 7 mg/kg/day. In some embodiments, cyclo-Hispro is administered to the mammal in an amount from about 3 to about 5 mg/kg/day. In some embodiments, cyclo-Hispro is administered to the mammal in an amount from about 7 to about 10 mg/kg/day. In some embodiments, cyclo-Hispro is administered to the mammal in an amount from about 0.5 to about 2 mg/kg/day. In some embodiments, cyclo-Hispro is administered to the mammal in an amount from about 0.2 to about 4 mg/kg/day. In some embodiments, cyclo-Hispro is administered to the mammal in an amount from about 0.8 to about 3 mg/kg/day. In some embodiments, cyclo-Hispro is administered to the mammal in an amount from about 1 to about 6 mg/kg/day.

In one embodiment for treatment of human beings, each tablet or capsule preferably contains about 1 to about 200 mg of zinc, preferably about 5 to about 50 mg zinc, and about 0.5 to about 200 mg of CHP, in addition to the pharmaceutically acceptable excipient or excipients. Thus, a preferred weight ratio of zinc cation to CHP is from about 1:100 to about 100:0.5. It is believed that compositions with these ratios of ingredients are effective in treating a wide range of mammals.

A third composition useful for treating preventing or delaying the onset of AD or dementia in a mammal includes both 1) thyroid hormone and 2) zinc and CHP. In one embodiment, a method of treating, preventing, or reducing AD or dementia in a mammal, said method includes administering at least once daily to the mammal a pharmaceutical composition comprising thyroid hormone, a zinc cation and anion, and cyclo-Hispro. However, the thyroid hormone, zinc salt, and cyclo-Hispro may also be administered in two or more compositions. In certain embodiments, the thyroid hormone is administered in a pharmaceutically effective amount to cause an increase in a serum level of thyroid hormone in the mammal and the zinc and cyclo-Hispro is administered to the mammal in a pharmaceutically effective amount to cause an increased serum level of IDE in the mammal. In some embodiments, the increased serum level of thyroid hormone is euthyroidic. In other embodiments, the increased serum level of thyroid hormone is hyperthyroidic.

Thyroid hormone, zinc, and CHP may be administered in amounts as described above with respect to the other compositions. In some embodiments, the thyroid hormone is administered to the mammal in an amount from about 1 to about 100 μg/day; the zinc cation is administered to the mammal in an amount from about 1 to about 100 mg/day; and the cyclo-Hispro is administered to the mammal in an amount from about 0.5 to about 50 mg/day. However, these values may vary in accordance with the ranges described above for the individual treatments. In some embodiments, the combination therapy may result in reduction of the amounts below.

Any of the above described amounts in relation to the any of the other embodiments, including other methods and compositions, may be used in formulating a treatment with thyroid hormone, zinc salt, and cyclo-Hispro.

The pharmaceutical compositions described herein are useful for the treatment of AD and/or dementia. In particular, AD can be treated by administering the composition in a quantity sufficient to increase memory. In addition, the pharmaceutical compositions described herein are useful for the treatment of metabolic syndrome.

Although other materials and methods similar or equivalent to those described herein can be used in the practice or testing of the present invention, the preferred methods and materials are now described.

Importance of Thyroxine in Neuronal Development

Without wishing to be bound by any particular theory, it is believed that thyroid hormone is required for normal neuronal development. However, even in patients with an apparent euthyroid status, central nervous system (CNS) specific hypothyroidism correlates clinically with AD. In addition, there is a genetic correlation between autoimmune thyroiditis and Down's syndrome (DS), with the strongest correlation in DS patients that manifest with AD pathology. Thus, there appears to be a direct relationship between thyroid hormone and AD neuropathology.

The supply of the active form of thyroid hormone in the brain, $T_3$, is primarily generated by the uptake and intracellular deiodination of $T_4$ by type 2 deiodinase (D2). Deiodinase type 3 (D3) catalyzes the conversion of $T_4$ and $T_3$ to their respective inactive metabolites, reverse $T_3$ and $T_2$. Solutes from the extracellular cerebral areas migrate into the cerebrospinal fluid (CSF). Total $T_3$ levels in CSF pools are lowered in AD patients (57.7 ng/dL in AD vs. 148.9 in normal), while the CSF reverse $T_3$ levels are significantly increased (12.6 ng/dL in AD vs. 6.1 in normal), indicating a possible increase in D3 activity in the AD brain. TGFβ, which is up-regulated in AD, positively regulates the D3 gene. Thus a localized hypothyroidism may exist even in apparent euthyroid patients due to impaired intracerebral thyroid hormone metabolism. Additionally, reverse $T_3$ is a competitive inhibitor of D2, which would result in an effective diminution of active cerebral $T_3$ levels in AD. Thus localized hypothyroidism in systemically normal presenting patients may be responsible for increasing Aβ plaque load in AD brain.

It now appears that a negative thyroid hormone response element in the APP gene may exist and can be utilized to lower Aβ expression in vivo. Furthermore, we have observed that when animals are made hypothyroid, APP gene expression is increased beyond normal euthyroid levels. Because localized hypothyroidism is observed in the central nervous system (CNS) of AD patients, presumably from an increase in metabolism of $T_4$ and $T_3$ to the inactive reverse $T_3$ and $T_2$ by type 3 deiodinase, it appears that a possible cause of AD is an increase in APP expression due to lack of negative regulation by thyroid hormone. This is reinforced by the fact that TGFβ levels are elevated in high pathology regions of the AD brain. TGFβ activates the type 3 deiodinase gene via a Smad dependent response element, leading to increased production of the enzyme and an increased rate of inactivation of both $T_3$ and $T_4$.

According to some embodiments, one aspect is not to attempt to treat AD by inducing severe hyperthyroidism in human patients to lower Aβ levels, but rather to return Aβ levels to normal or slightly lower by returning the associated CNS hypothyroidism to a normal euthyroid range, or very slightly above, by hormone replacement. Any further required reduction in Aβ would be accomplished by activating insulin-degrading enzyme activity as also described herein.

Thyroid hormone regulates gene expression in both positive and negative fashions. Positive thyroid response elements (TREs) are more readily characterized than negative TREs. In a positive TRE in the absence of hormone, corepressors SMRT and N—CoR are recruited by the receptor and mediate basal transcription levels. Thyroid hormone binding to receptor results in a dissociation of corepressors and an association of coactivators, resulting in a reversal of inhibition and activation of transcription. Negative TREs have been identified in genes encoding growth hormone, TSH beta, PC1, c-myc, alcohol dehydrogenase, PC2, type 1 deiodinase, and the transcription factor E2F-1.

An element in the first exon of the APP gene which binds heterodimers of thyroid hormone receptor and retinoid X receptor has been discovered. However, by itself this element is unable to confer negative regulation by thyroid hormone on a reporter construct in transfection assays. The APP gene is positively regulated by TGFβ, and an increase in TGFβ levels is observed in brain and cerebrospinal fluid (CSF) of AD patients. TGFβ isoforms transduce their biological signal through the serine-threonine kinase receptors TβR-I and TβR-II, which activate the Smad transcription factor cascade. Smad-dependent regulation of gene transcription is modulated by interaction with transcriptional co-activators and co-repressors. TGFβ treatment increases Smad3-Smad4-Sp1 complex formation and the binding of these transcription factors to the response element of the APP gene. Smad3 and Smad4 bind to the +54/+74 region of the APP gene, while Sp1 requires the +64/+83 region for binding. Interestingly, thyroid hormone receptor alpha (TRα binds to the +75/+96 region, indicating overlap between the Sp1 and TRα binding sites. Because Smad3, Smad4, and Sp1 bind as a complex, thyroid hormone may negatively regulate the expression of the APP gene by interfering with this binding and therefore with the positive regulation of this gene induced by TGFβ. This may be accomplished by an increase in thyroid hormone receptor-retinoid X receptor heterodimer binding to the APP element upon thyroid hormone treatment, displacing the Smad and Sp1 binding induced by TGFβ. This hypothesis should prove easily testable by transfection and gel shift assays. The role of TGFβ in AD may be somewhat underappreciated. Mice transgenic for the TGFβ gene over-express this gene and demonstrate high plaque load. Increased levels of TGFβ and other cytokines are observed in AD patients. TGFβ also positively regulates the type 3 deiodinase gene, causing an increase in the deactivation of $T_4$ and $T_3$, and resulting in hypothyroidism. This is precisely what is observed in the CSF of AD patients, and also accounts for the potential lack of negative regulation of the APP gene by $T_3$ in this disease.

Figure 7:
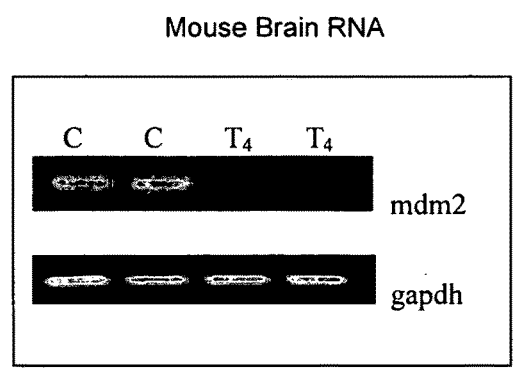
FIG. 7 illustrates reduced mdm2 gene expression in huAPP mice treated with T4.
Figure 9:
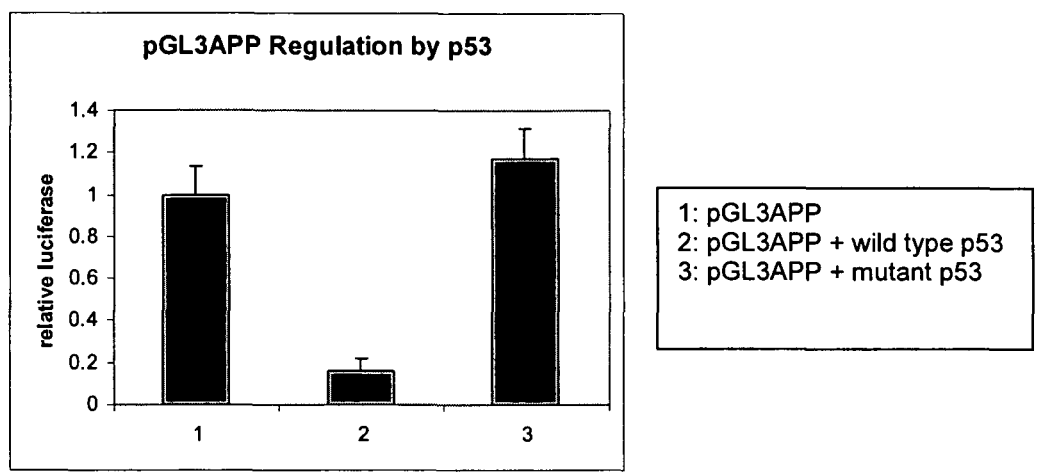
FIG. 9 illustrates that wild type p53 confers negative regulation on APP construct.

There is an element in the upstream region of the APP gene between −320 and +42 which confers negative regulation by p53 on a luciferase reporter construct in transfection assays (FIG. 9). The p53 protein binds to the mdm2 protein and is targeted for degradation by this interaction with mdm. Levels of p53 are therefore inversely affected by the amount of mdm2 production. We have observed that mdm2 gene expression is negatively regulated by thyroid hormone in the brain (FIG. 7). Lowering mdm2 expression would diminish the targeted degradation of p53, thereby increasing steady-state levels of p53. This would allow for an increase in the amount of negative regulation of the APP gene by p53. Therefore, a second potential mechanism for the negative regulation of APP expression exists indirectly via the effect of thyroid hormone on the mdm2 gene. This mechanism is relatively easy to test by determining the levels of free and mdm2-complexed p53 in mouse brain following hormone treatment.

Importance of Cyclo(His-Pro) in Reducing Aβ

It has now been discovered that pharmaceutical compositions comprising zinc and CHP may used to treat, prevent, or delay the onset of AD or dementia in mammals. Without wishing to be bound by any particular theory, it is believed that the combination of zinc and CHP causes increased activation of insulin-degrading enzyme (IDE) which degrades Aβ peptide, as well as insulin.

One particular drug treatment for AD or dementia includes administering a pharmaceutically effective amount of zinc and cyclo-His-Pro (CHP). Such drug treatment may be used to activate IDE at the enzyme level. IDE is a zinc containing enzyme, and increasing the ratio of holoenzyme to apoenzyme may increase activity without activating IDE gene expression. Furthermore, CHP increases the absorption of zinc through the intestine and into tissue, presumably by its ability to chelate zinc. It also has been demonstrated to be non-toxic to humans and mice in our previous studies.

It has been observed that insulin-degrading enzyme (IDE) degrades both insulin and Aβ. In addition, patients with insulin-resistant diabetes have higher insulin levels and higher levels of Aβ. Discovery of a method to increase IDE activity should therefore decrease Aβ steady state levels and decrease plaque load. To this end we have developed a method to increase Aβ degradation in transgenic mouse brain based on a method developed here to decrease insulin levels.

As shown in our previous studies, CHP+zinc (as in U.S. Pat. No. 5,834,032 and herein incorporated by reference in its entirety) has been utilized to lower insulin levels as a method for treating insulin-resistant diabetes. CHP is a metabolite of thyrotropin-releasing hormone (TRH), but is also produced directly from amino acid or peptide sources. CHP levels in diabetic subjects are significantly lower than in non-diabetic patients. CHP alone does not decrease insulin levels, however CHP+zinc decreases insulin levels in a concentration dependent manner relative to the amount of zinc. CHP chelates zinc, stimulating zinc intestinal absorption and uptake in muscle tissues.

Combination Thyroid Hormone & Zinc+CHP Treatment

It is believed that pharmacological intervention with thyroid hormone, CHP+Zn, or the combination of thyroid hormone and CHP+Zn causes one or more of the following effects in mammals: enhanced IDE activity, Aβ clearance, decreased Aβ plaque load, and enhanced cognition. This is supported by data that shows that CHP+Zn enhances brain IDE activity resulting in a significant decrease in both soluble and insoluble levels of Aβ 1-40 and 1-42; and that T4 therapy decreases APP mRNA and APP protein; and decreases total levels of Aβ 1-40 and 1-42.

The invention is further described in terms of the following experimental data which are intended for the purpose of illustration and not to be construed as in any way limiting the scope of the present invention, which is defined by the claims.

EXPERIMENTAL DATA

Thyroid Hormone Treatment

A. Effects of T3 on APP Secretion in Human Neuroblastoma Cells

We have tested the ability of triiodothyronine (T3) and thyroxine (T4 to down regulate APP gene expression. In a first study, we determined the ability of triiodothyronine ($T_3$) to down-regulate APP isoform secretion in SH-SY5Y and LA-N-5 human neuroblastoma cell lines, and in NHNP neuronal progenitor cells. Shown in FIG. 1 is a western blot demonstrating the effect of thyroid hormone treatment on APP secretion in both differentiated (+RA) and undifferentiated (−RA) SH-SY5Y human neuroblastoma cells following 24 hours of treatment. As is shown in FIG. 1, all tested human cell lines demonstrated a similar negative hormonal regulation of APP secretion in a concentration dependent manner.

B. Effects of T4 on Normal Mice

In a second study, we discovered that thyroid hormone treatment down-regulates the expression of the APP gene in normal mice. In this study, we extended our tissue culture observations to brain tissue of normal mice by inducing hyperthyroidism and hypothyroidism in these animals. Three groups of nine mice were treated as follows: in the control group, sham pellet surgeries with normal chow; in the hyperthyroid group, implantation of a thyroid hormone ($T_4$; L-thyroxine) 21-day sustained release pellet (0.025 mg/pellet, Innovative Research of America, Sarasota, Fla.) with normal chow; in the hypothyroid group, sham pellet surgery with iodine-deficient chow containing 0.15% propylthiouracil (Harlan Teklad, Madison, Wis.). On day 21, animals were killed, whole brains were removed and hemisected for protein and RNA analysis, and serum was collected for $T_4$ analysis. Hyperthyroidism was confirmed by demonstrating increased serum levels of $T_4$ in hormone treated mice (10.73±1.27 ug/dl, mean±SD) vs. control mice (4.32±0.30 ug/dl). Hypothyroidism was confirmed by demonstrating decreased serum levels of $T_4$ in propylthiouracil treated mice (0.03±0.02 ug/dl) vs. control mice (4.32±0.30 ug/dl).

Figure 2:
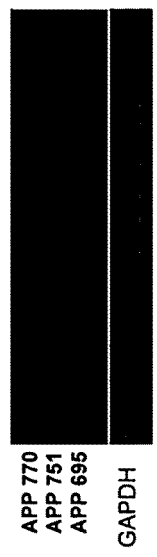
FIG. 2 illustrates RT-PCR analysis of T4 on the expression of APP mRNA levels in normal mice.
Figure 3:
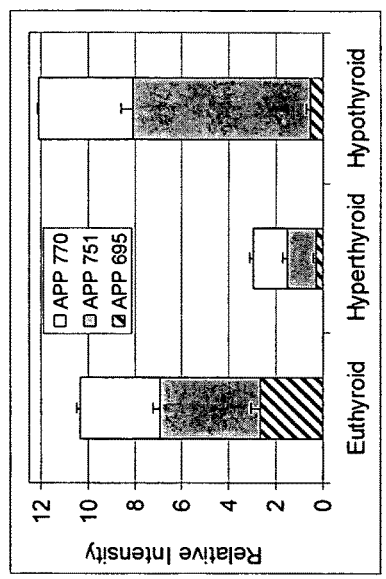
FIG. 3 illustrates the relative intensities of the RT-PCR analysis of FIG. 2.

In FIG. 2, a RT-PCR analysis reveals that, in hyperthyroid mice, APP mRNA levels were decreased (lanes 2 and 3) when compared to control animals (lane 1). Conversely, hypothyroid mice showed increased levels of APP 751 mRNA (lanes 4 and 5) when compared with controls. The relative intensities are further shown in FIG. 3. These results suggest that thyroid hormone also confers negative regulation on mouse APP gene expression in vivo.

Figure 4:
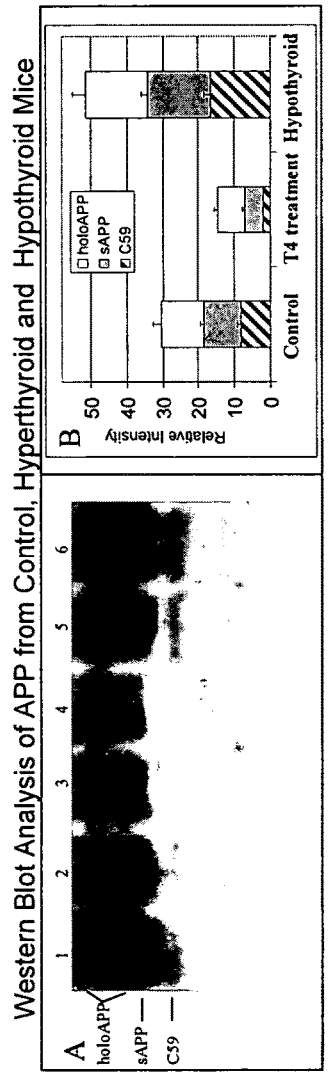
FIG. 4 is a western blot of hemisected brain extracts of the huAPP mice used in the experiment.

In FIG. 4, Western blots were performed utilizing anti-APP antibody on protein from the hemisected brain extracts. Hyperthyroid animals (lanes 3 and 4) demonstrated an overall decrease in expression of APP isoforms, whereas hypothyroid animals (lanes 5 and 6) showed increased expression of APP isoforms relative to euthyroid animals.

C. Reduced Levels of Aβ by Treatment of T4 on HuAPP Mice

In another study, we discovered that thyroid hormone down-regulates Aβ 1-40 and 1-42 in mice transgenic for the human APP gene. Since normal mice do not develop Aβ containing plaques or exhibit other AD specific neuropathologies similar to humans, we determined if mild hyperthyroidism could regulate Aβ synthesis in mice transgenic for the human APP gene. R1.40 human APP transgenic mice contain the entire human APP gene carried on a yeast artificial chromosome. R1.40 mice develop extracellular Aβ deposits and exhibit neuropathology resembling human Alzheimer's disease.

Mice used in these studies carried the complete human APP gene (huAPP), including the 5' upstream promoter region, inserted into a yeast artificial chromosome (YAC) construct and are referred to as huAPP-YAC transgenic mice (R1.40 strain). The huAPP gene in these mice contained the Swedish mutation and is expressed in high pathology brain regions.

Figure 5:
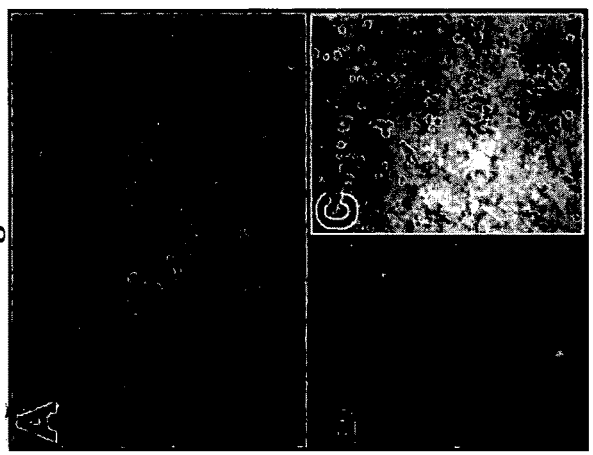
FIG. 5 shows microscopic images of frozen sections of brain from huAPP mice. A shows Aβ staining using the monoclonal antibody 6E10. B shows thioflavin S staining of the hippocampus. C shows GFAP positive astrocytes in the cortex by using a haematoxylin counterstain.

As shown in FIG. 5, 18 month old huAPP mouse brains contain Aβ- and Thioflavin S positive plaques and contain reactive astrocytes. HuAPP mice show low to no AD pathology at 9 months but high pathology in the second year of life (14-18 months) including high expression of all huAPP isoforms (770, 751, 695), soluble Aβ (40 and 42), Aβ positive and Thioflavin S positive plaques, increased oxidative stress, robust inflammation, cerebrovascular changes, cognitive dysfunction and marked presenilin influences, making this animal model ideal for APP gene regulation and processing studies as they relate to neuropathology.

Frozen sections from huAPP mice prepared as described in the following: We will quick freeze the left brain hemispheres of sacrificed mice, section them using a cryostat, thaw mount, and then refreeze them at −80° C. for future use. Thioflavin-S staining: Fixed sections will be soaked in 0.25% potassium permanganate solution for 20 min, washed in water, bleached for 2 minutes, washed in water, blocked in 30% H2O2 for 20 min, placed in 0.25% Acetic acid solution for 5 minutes, rinsed in water, then incubated in thioflavin S for 3-5 min. Slides are then mounted using glycerin jelly. 10× digital images are taken on a Zeiss Axioskop 2 plus microscope with fluorescence and processed by Axiovision software. Images are imported into ImageJ software for analysis. Immunohistochemistry: Immediately prior to immunostaining, sections will be fixed in 1:1 methanol:acetone for 10 min at −20 OC; treated for 5 min in a 0.5% H2O2 1:1 methanol:PBS solution to inhibit endogenous peroxidase, and then treated with 3% horse serum for 2 hours to block non-specific background. Sections are then be incubated with the primary antibody 6E10 recognizing Aβ fragment 1-17 (Signet) which has previously been shown to detect plaques in these mice (see FIG. 1 A). Bound antibodies are detected using ABC staining kits (Vector). 100-400× digital images will be taken on a Zeiss Axioskop 2 plus microscope with fluorescence and processed by Axiovision software. Images will be imported into ImageJ software for analysis. As is shown in FIG. 5, these sections show Aβ staining using the monoclonal antibody 6E10 (A; CA1 region of hippocampus), Thioflavin S positive plaques (B; CA1 region of hippocampus), and GFAP positive astrocytes (C; cortex) (haematoxylin counterstain).

Figure 6:
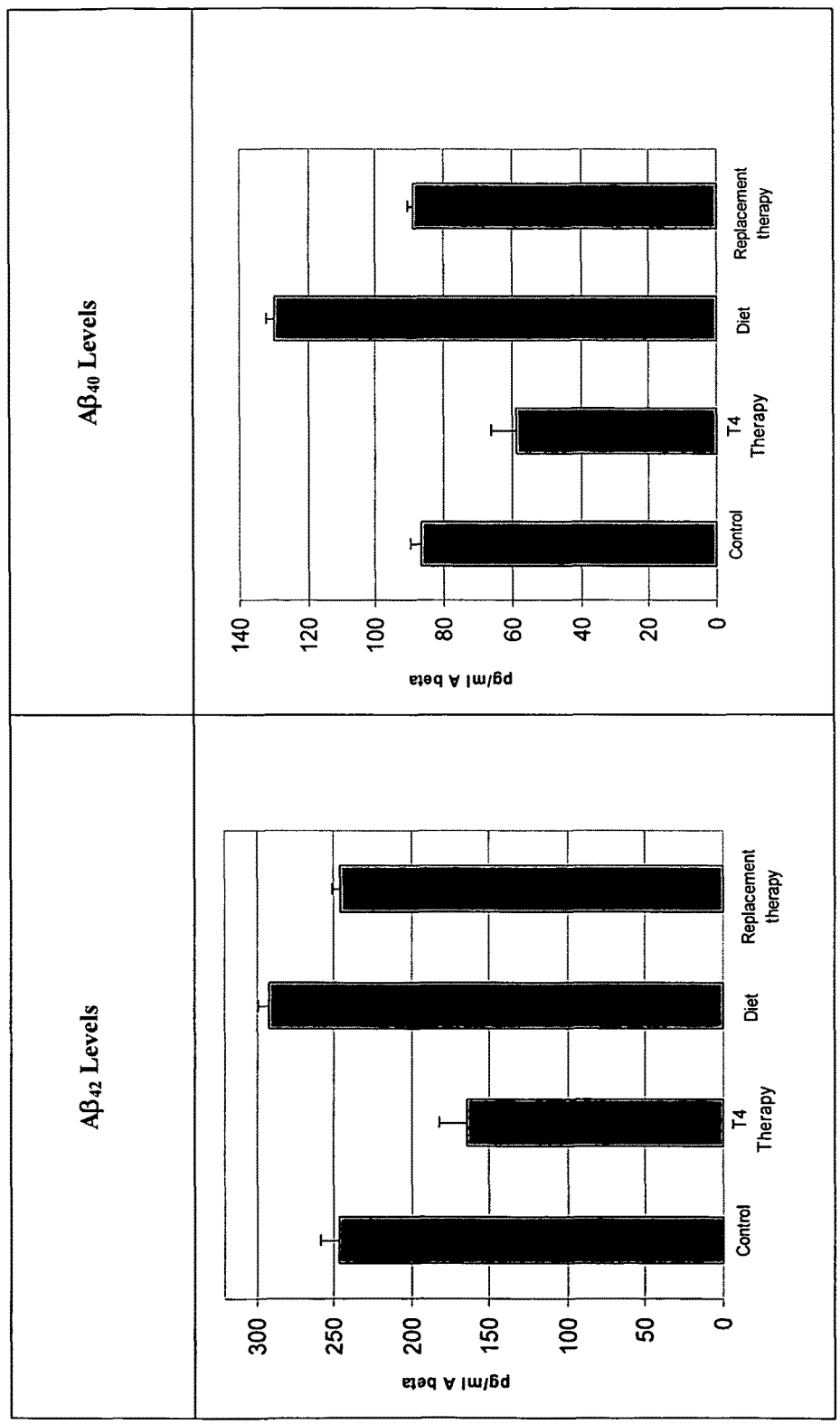
FIG. 6 illustrates the reduction of $A\beta_{40}$ and $A\beta_{42}$ treating huAPP (R1.40) mice with T4 and replacement therapy.

R1.40 mice were implanted with $T_4$ containing slow release pellets for three weeks and ELISA specific for human Aβ was performed utilizing normalized protein from mouse brain cytosols. We observed a 30% decrease in human Aβ 1-42 levels and a 25% decrease in Aβ 1-40 levels in mice treated for three weeks with $T_4$. Additionally, mice first made hypothyroid for three weeks with an iodine-deficient PTU diet, and then replaced with $T_4$ to reverse hypothyroidism, showed Aβ levels similar to normal mice, while hypothyroid animals demonstrated an increase in brain Aβ levels as shown in FIG. 6. Brain levels of total human Aβ42 and Aβ40 were significantly decreased after treatment with T4 as measured by ELISA in huAPP transgenic mice. Thus, it has been shown that low level thyroid hormone therapy substantially decreases human Aβ40 and Aβ42 levels in both normal and hypothyroid transgenic mice (n=9 animals per group ±SD). This is significant since AD patients, which show normal T4 serum concentrations, present with CNS specific hypothyroidism, suggesting that modest treatment of T4 as a replacement therapy could decrease Aβ production.

Serum $T_4$ RIA assays were performed to confirm thyroid hormone status (Table 1).

TABLE 1

| Radioimmunoassay for Total Thyroxine | |
|---|---|
| control | 4.77 ± 0.24 ug/dl |
| hyperthyroid | 9.43 ± 1.27 ug/dl |
| hypothyroid | 0.02 ± 0.02 ug/dl |

Based on the aforementioned data, it appears that the negative regulation of the APP gene by thyroid hormone observed in tissue culture and in normal mouse brain also extends to human APP gene expression and resultant Aβ levels in transgenic mice.

D. Reduced mdm2 Gene Expression Correlates with Treatment of T4 on HuAPP Mice In another study, RNA extracted from brain of control and thyroxine treated mice was utilized to quantify mdm2 levels under euthyroid and hyperthyroid conditions. FIG. 7 demonstrates that mdm2 transcript content in individual mouse brain declined following 21 day pellet implantation supporting our earlier observations in tissue culture experiments.

Figure 8:
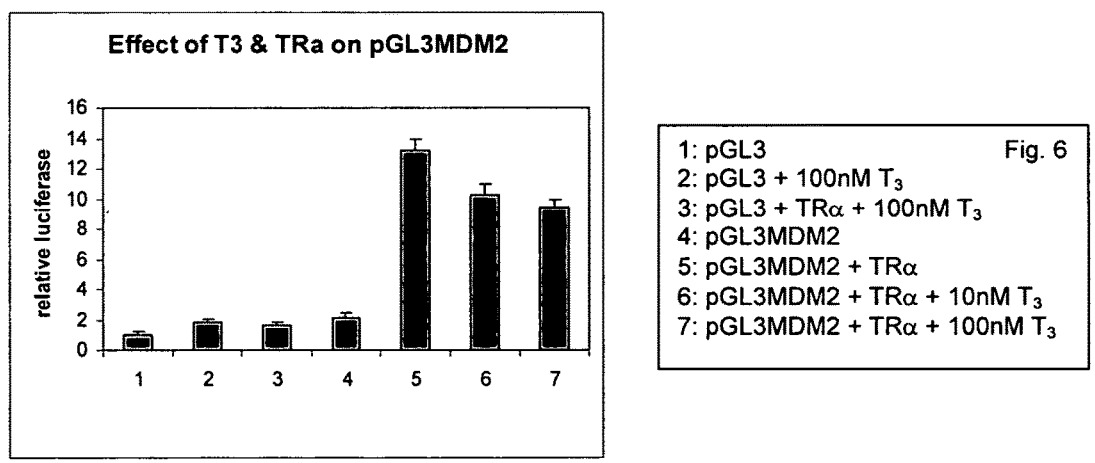
FIG. 8 illustrates the effects of treatment with T3 on expression of the pGL3 promoter in the first intron of the mouse mdm2 gene.

In order to evaluate the direct effect of thyroid hormone on mdm2 gene expression, we cloned the +356/+755 region from the first intron of the mouse mdm2 gene into pGL3-Promoter vector (pGL3MDM2) for use in transfection assays. This region contains an element which binds monomers and homodimers of TRα, in addition to heterodimers of TRα and RXRβ. As shown in FIG. 8, transfection analysis in both LA-N-5 neuroblastoma cells and p53 negative HCC1806 breast cancer cells revealed this region conferred negative regulation of reporter expression onto the pGL3 promoter.

E. p53 Tumor Suppressor Negatively Regulates APP Gene

In another study, it was discovered that the p53 tumor suppressor negatively regulates the APP gene. The −322/+42 region of the APP gene was cloned into pGL3 to form a reporter construct. This region includes the APP promoter region and potential five prime enhancer sequences. As shown in FIG. 9, co-transfection of this construct with wild type and mutant p53 demonstrated that wild type p53 conferred negative regulation on the APP construct. Mdm2 binds to p53 and targets its degradation, thereby lowering steady-state p53 levels. Because thyroid hormone treatment negatively regulates mdm2 expression in brain, presumably through an element in the sequence identified in FIG. 7, less mdm2 will be available to target p53 for degradation. Therefore thyroid hormone treatment may effectively increase p53 levels, leading to an increase in negative regulation of the APP gene and lower APP transcript levels as observed in FIGS. 2 & 3.

F. T4 Treatment in huAPP Mice Results in Enhanced Spatial Memory

In another study, it was shown that Thyroid hormone treatment enhances spatial memory in huAPP transgenic mice. To test this, we employed a Morris water maze using a circular pool with movements and data being captured using the SDI SMART video tracking system (San Diego Instruments). Experiments were run daily for 14 days between 8 a.m. and noon, alternating between control and treated mice. The 7 day acquisition phase consisted of four 60 second trials per day with an inter-trial interval of 2 minutes. Animals were introduced into the pool facing the wall, alternating between the east and west positions. A trial was stopped when the animal reaches the platform, and was allowed to remain on the platform for 15 seconds. On day 8, learning was evaluated with a single 60-second probe trial in which the platform is removed, and animals were introduced into the maze at the east position. On days 9 and 10, in order to reorient the mice to the north position of the platform, animals repeated four 60 second trials per day as in the acquisition phase. Days 11-13 constituted the reversal phase in which the platform position was changed to the south position in the diagonally opposite quadrant. On day 14, mice were given four 60 second cue trials in which a black and white striped circular platform positioned in the south quadrant is raised 1.5 cm above the water and visibly marked with a flag. Results were averaged across the 4 trials/day and expressed as a daily mean. Dependent variables were latency and distance to reach the platform. Repeated measures analyses of variance (ANOVA) were separately used to analyze the acquisition phase (days 1-7) and the reversal phase (days 11-13), using drug treatment as a between subjects variable and days as within-subjects variable. Post hoc comparisons are by Tukey's multiple comparison test.

Figure 10:
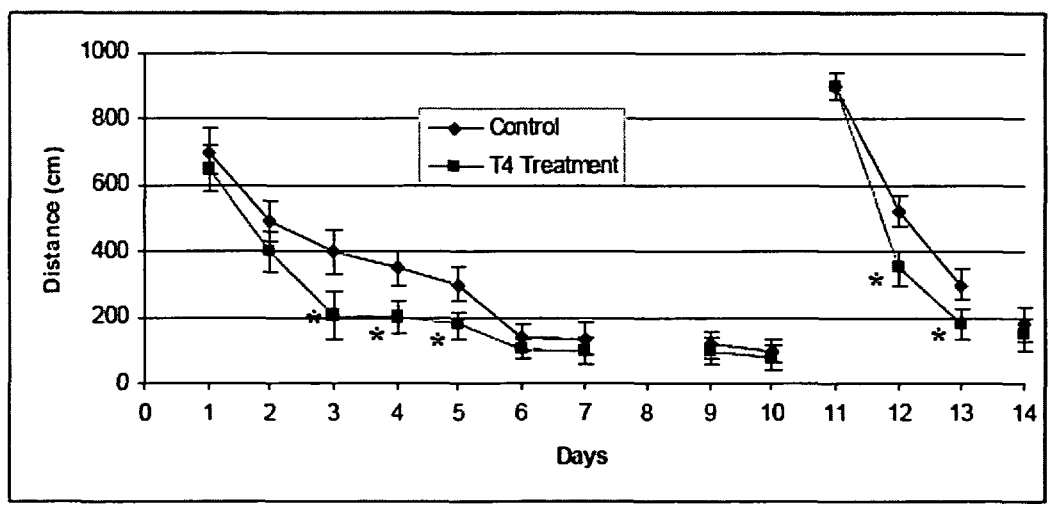
FIG. 10 illustrates the results of a Morris water maze test on huAPP transgenic mice treated with T4 vs. control animals.
Figure 11:
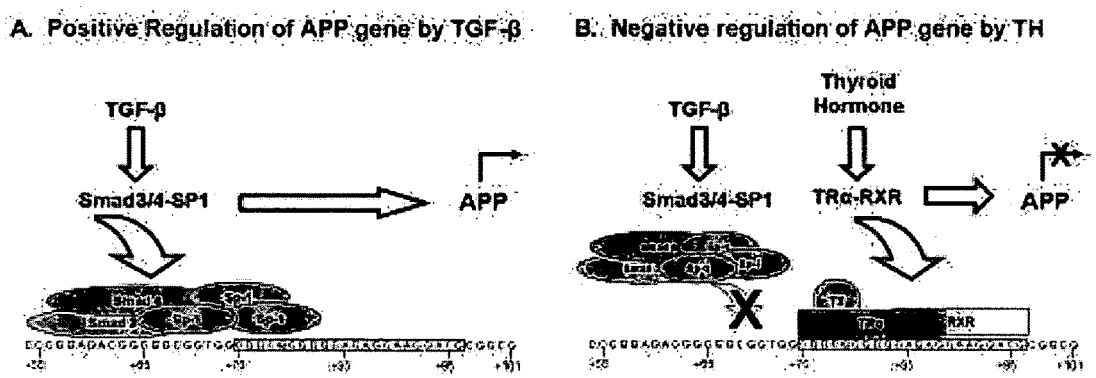
FIG. 11 illustrates that binding transcription factor complexes Smad3, Smad4, Sp1 to response elements may be blocked by treatment of thyroid hormone thereby preventing translation of APP protein.

9 month old huAPP transgenic mice were divided into 2 groups of 3 animals each and treated as follows: control, sham pellet surgeries; T4, implantation of a thyroid hormone ($T_4$; L-thyroxine) 90-day sustained release pellet (0.1 mg/pellet) (Innovative Research of America, Sarasota, Fla.). At 12 months, animals were subjected to the Morris Water Maze and the mean distance to the platform was measured on days 1-7, probe on day 8, repetition of acquisition on days 9-10, reversal phase on days 11-13, and a visible platform cue phase on day 14. As shown in FIG. 10, significant improvement in spatial memory is seen in days 3-5, and 12-13 as determined by the Tukey multiple comparison test (n=3 animals per group ±SEM).

F. Prophetic Examples and Testing

1a. Titrate Thyroid Hormone Levels in Transgenic Mice Versus Degree of Soluble Cytosol and Membrane Aβ1-40 and 1-42 to Determine Optimal Response Versus Dose Transgenic mice are treated by implantation with four concentrations of sustained 90 day $T_4$ release pellets. In order to optimize the response, a 0.10 mg pellet is required to approximate the same dose per time as a 21 day 0.025 mg pellet. We implant thyroxine 90 day release pellets at the following doses: 0.5 mg/pellet, 0.1 mg/pellet, 0.025 mg/pellet, and 0.006 mg/pellet. Following 90 days treatment, animals are sacrificed and brains dissected for protein extraction and RNA isolation. High pathology regions (frontal cortex and hippocampus) are extracted separately. Brain is homogenized in 50 mM Tris, 0.2 M sucrose, pH 7.4, and protein fractionated into nuclear, membrane, and cytosolic fractions. Membrane and cytosolic fractions are used for ELISA to quantify both human Aβ 1-40 and 1-42. Biosource ELISA kit is specific for human Aβ, and also distinguishes 1-40 from 1-42. Additionally, RNA is isolated by the guanidinium thiocyanate/phenol extraction method (49), and human specific primers are used for RT-PCR to measure APP-695, -751, and -770 transcripts in treated and untreated mice. Aβ levels and APP transcript levels are correlated with $T_4$ treatment dose. Furthermore, serum total $T_4$ is quantified by RIA from all treatment groups and levels are correlated with human specific Aβ peptide and APP transcript levels from treated and untreated mice. Data is analyzed, and an appropriate $T_4$ pellet dose decided upon for long term treatment.

1b. Utilize Optimized Thyroid Hormone Dose for Extended Treatment and Quantity the Ability of this Treatment to Inhibit Plaque Formation Because plaque formation is the result of Aβ aggregation, presumably decreasing Aβ production will decrease plaque formation. In order to determine if sustained treatment of pre-plaque mice can inhibit plaque formation, human APP expressing transgenic mice (strain R1.40), (12 control, 12 treated) are treated with sustained release $T_4$ pellets, as maximized above, between 9 and 16 months of age, as this is the time during which we observe plaque formation in these mice. Animals are implanted every 3 months with a 90 day sustained release pellet. At 13 and 16 months of age, animals are terminated, serum is taken for $T_4$ RIA analysis, and the brain is divided for histology and protein extraction.

To determine plaque load, brain hemispheres is dissected out and quick frozen, cut using our cryostat, thaw mounted, and frozen at −80° C. for future use. Thioflavin-S staining: Fixed sections are soaked in 0.25% potassium permanganate solution for 20 minutes, are washed in water, are bleached for 2 minutes, are washed in water, are blocked in 30% hydrogen peroxide for 20 minutes, are placed in 0.25% acetic acid for 5 minutes, are rinsed in water, then are incubated in thioflavin S for 3-5 minutes. Slides are then mounted in glycerin jelly. 10× digital images are taken on a Zeiss Axioskop 2 plus microscope with fluorescence and processed by Axiovision software. Images are imported into ImageJ software for analysis. Immunohistochemistry: Immediately prior to use, sections are fixed in 1:1 methanol: acetone for 10 min at 20° C. Endogenous peroxidases are blocked for 5 min in a 0.5% hydrogen peroxide 1:1 methanol:PBS solution and nonspecific background are blocked with 3% horse serum for 2 hours. Sections are incubated with primary antibodies against various Aβ fragments (Signet, Calbiochem, Santa Cruz) to detect plaques. Visualization is done by ABC staining kit (Vector). 10× digital images are taken on our Zeiss Axioskop 2 plus microscope with fluorescence and processed by Axiovision software. Images are imported into ImageJ software for analysis. Plaque load level are compared between $T_4$ treated and control mice. Additionally, plaque load is separately quantified in high pathology regions of the brain including frontal cortex and hippocampus (CA1-CA3, Dentate, etc.).

ELISA: Levels of Aβ 1-40 and 1-42 is quantified and compared with controls following this extended treatment in order to correlate their decrease with any changes in plaque formation observed with this treatment. Aβ levels are quantified during the treatment so they can be accurately related to plaque load. Upon sacrifice, brain hemispheres will be homogenized and fractionated as above for protein analysis. Cytosol and membrane fractions are quantified for Aβ 1-40 and 1-42 by ELISA as described by the manufacturer (Biosource). ELISA data is analyzed by ANOVA and Newmans-Keuls t-test.

RNA Quantification: We quantify the changes in human APP transcripts (770, 751, and 695) following hormone treatment. We utilize human specific primers to quantify changes in human APP transcripts expressed in R1.40 transgenic mice. Extracted RNA is utilized for cDNA synthesis and PCR is performed. PCR products are electrophoresed and quantified on an Alpha Innotech gel documentation system. APP transcript level are correlated with Aβ and plaque load.

1c. Characterize Putative Thyroid Hormone Response Elements in the APP Gene

The +54/+83 region of the APP gene confers positive regulation by TGFβ onto luciferase-expressing reporter constructs and binds the TGFβ induced Smad-Sp1 complex (32). The +79/+96 region of the APP gene binds heterodimers of thyroid hormone receptor and retinoid X receptor, indicating some overlap. It is believed that thyroid hormone negatively regulates the APP gene by repressing the positive regulation of the APP gene by TGFβ. TGFβ levels are increased in the AD brain and CSF.

Double-stranded oligonucleotides representing the +48/+108 region of the APP gene flanked by two XhoI restriction sites are ligated into the pGL3-Promoter vector (Promega) containing an SV40 promoter sequence for use in transfection studies. Mv1Lu cells, which are responsive to TGFβ signaling, are utilized for transfections. In order to evaluate the effect of thyroid hormone and its receptor on repression of TGFβ induction, appropriate transfection combinations are utilized. Cells are transfected with Smad3, Smad4, and Sp1 under control and TGFβ treatment to confirm TGFβ induction. Cells are further transfected with TRα, RXR, Smad3, Smad4, and Sp1 with and without TGFβ, both in the presence and absence of thyroid hormone. Experiments are repeated with TRβ in place of TRα.

Gel shift assays are performed to determine if TRα and TRβ can interfere with transcription factor complex Smad3/Smad4/Sp1 binding to the response element both in the presence and absence of thyroid hormone. Oligonucleotides representing the double-stranded regions described above are end labeled with [α-$^{32}$P]dCTP using the Klenow fragment of DNA polymerase. Smad3, Smad4, TRα, RXR, TRβ, and Sp1 protein are generated by adding appropriate respective plasmids to a Promega transcription and translation system. Following incubation for 20 min at 37° C. in binding buffer, complexes are resolved on a 5% polyacrylamide gel containing TBE. Gels are dried, exposed to a Molecular Dynamics screen, and visualized on a Molecular Dynamics Phosphorimager. The ability of TRα/RXR and TRβ/RXR heterodimers to inhibit Smad3/Smad4/Sp1 binding is evaluated in gel shift assays both in the presence and absence of thyroid hormone. Supershift assays are performed to confirm the data. Nuclear extracts and transcription factor/receptor antibodies are also utilized in gel shift experiments if data from TNT generated proteins is not easy to interpret.

The upstream region of the APP gene containing the negative p53 response element is identified by performing transfections with p53 expression vector and elements representing smaller regions of the APP upstream region. Oligonucleotides representing candidate elements are ligated into pGL3, and the negative element are further validated by utilizing oligonucleotides representing mutations to this region in transfection assays and gel shift assays. Gel shift assays are performed, using p53 protein generated in a Promega TNT system.

Levels of steady-state p53 protein in both cytosol and nuclei are determined in mouse brain from control and thyroid hormone treated animals. As thyroid hormone treatment lowers mdm2 levels in mouse brain, and mdm2 targets p53 for degradation, it is believed that lower mdm2 levels will allow for higher steady-state p53 protein in hormone treated brain. This may down-regulate APP expression through a p53 negative response in the APP gene. Protein extracts from cytosolic and nuclear fractions are western blotted under hormone treated and control conditions to quantify potential changes in expression. Furthermore, pulldown assays are performed on mdm2-p53 complexes extracted under non-denaturing conditions to determine if less p53 is being targeted for protease degradation following thyroid hormone treatment.

II. Zinc & CHP Treatment

A. Reduced Levels of Aβ by Treatment of Zn+CHP on HuAPP Mice

Figure 12:
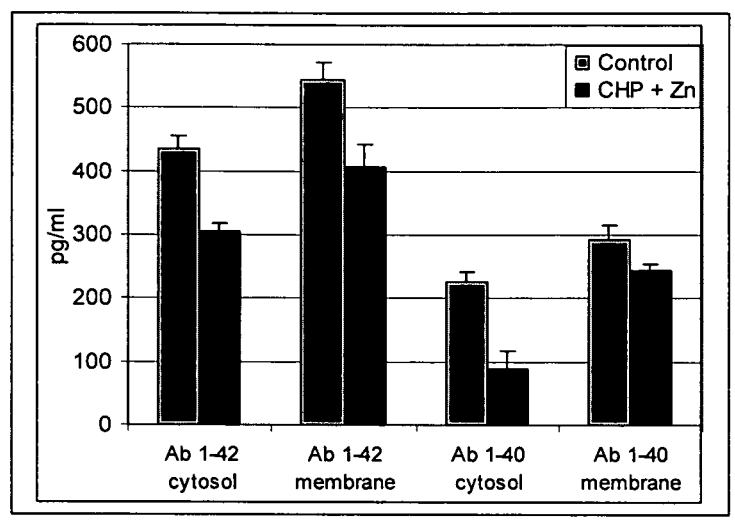
FIG. 12 illustrates the effects of CHP and Zn on cytosolic and membrane levels of $A\beta_{40}$ and $A\beta_{42}$ in huAPP mice.

According to our studies, CHP in combination with a zinc salt decreases Aβ 1-40 and 1-42 in mice transgenic for human APP. We treated human APP transgenic mice with 1.0 mg/ml CHP and 10 mg/L Zn in their drinking water for 5 weeks and quantified human Aβ 1-40 and 1-42. As shown in FIG. 12, CHP and Zn caused a 60% reduction in cytosolic Aβ 1-40 and a 25% reduction in Aβ 1-42 over the five week period.

B. Increased IDE Levels of Aβ by Treatment of Zn+CHP on HuAPP Mice

Figure 13:
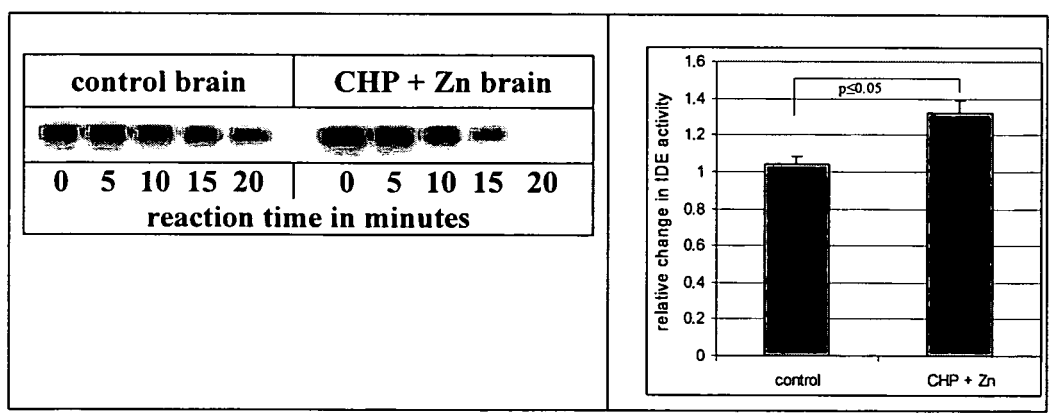
FIG. 13 illustrates both the reaction time and the relative effects of CHP and Zn on IDE activity.

Additionally, an increase in IDE enzyme activity was also observed as shown in FIG. 13. IDE contained within cytosolic brain samples from control animals require more than 20 minutes to degrade radiolabeled insulin whereas CHP+Zn treated animals show enhanced IDE activity as 100% of insulin is degraded within 20 minutes (left). Quantitative measures show that there is an approximately 30% enhancement of IDE activity due to CHP+Zn therapy after treatment (right) (n=6 animals per group ±SD).

Figure 14:
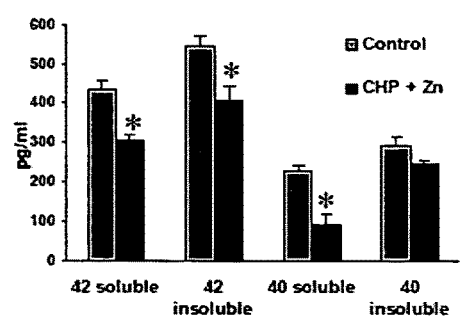
FIG. 14 illustrates the reduction of soluble and insoluble $A\beta_{40}$ and $A\beta_{42}$ by treatment of huAPP mice with CHP and Zn.

C. Reduced Soluble $A\beta_{40}$ and $A\beta_{42}$ by Treatment of Zn+CHP on HuAPP Mice It has also been discovered that brain levels of soluble and insoluble human $A\beta_{42}$ and $A\beta_{40}$ are significantly decreased after treatment with CHP+Zn in huAPP transgenic mice as measured by ELISA. As shown in FIG. 14, we demonstrated marked reduction in both soluble and insoluble $A\beta_{40}$ and $A\beta_{42}$ in transgenic animals treated with 1.0 mg/L CHP+10 mg/L Zn, while treatment of animals with Zn or CHP alone showed no significant changes in $A\beta$ levels when compared with control (data not shown), (n=9 animals per group ±SD; *=p≤0.05).

D. Zn+CHP Treatment in huAPP Mice Results in Enhanced Spatial Memory

Figure 15:
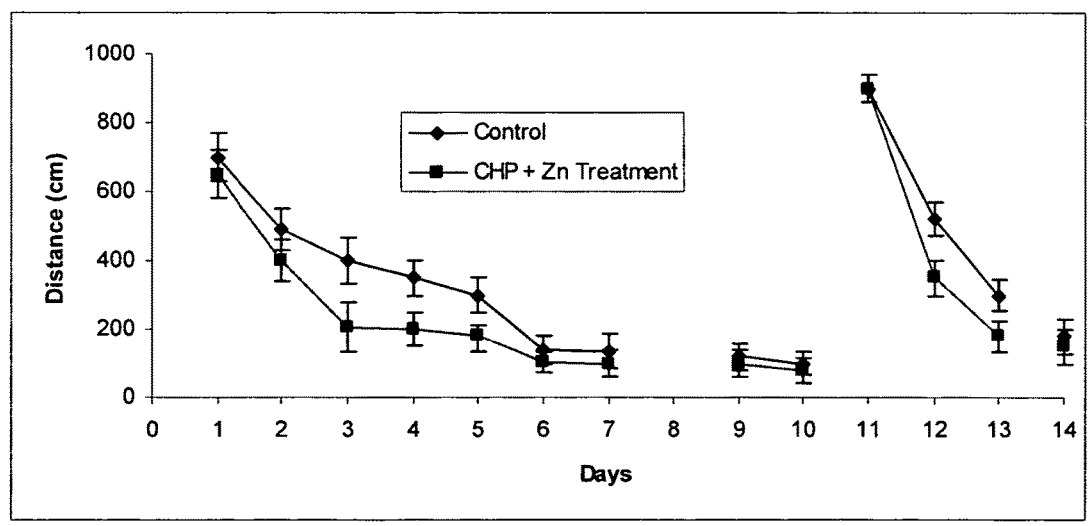
FIG. 15 illustrates the results of a Morris water maze test on huAPP transgenic mice treated with T4 vs. control animals.

In another study (FIG. 15), it was shown that CHP+Zn treatment enhances spatial memory in huAPP transgenic mice. HuAPP transgenic mice (9 months of age) were divided into 2 groups of 3 animals each and treated as follows: in the Control group, animals were given access to $H_2O$ alone ad libitum; in the CHP+Zn group, animals were given access to 1.0 mg/L CHP+10 mg/L Zn in $H_2O$ ad libitum. At 12 months, animals were subjected to the Morris Water Maze (as described above) and the mean distance to the platform was measured on days 1-7, probe on day 8, repetition of acquisition on days 9-10, reversal phase on days 11-13, and a visible platform cue phase on day 14. Significant improvement in spatial memory is seen in days 3-5, and 12-13 as determined by the Tukey multiple comparison test (n=3 animals per group ±SEM).

This data show that when zinc levels were maximized, and 10 mg/L Zn and 1.0 mg/L CHP was included in the drinking water of transgenic mice containing the human APP gene, both cytosoloic $A\beta$ 1-40 and 1-42 were decreased by 60% and 30% respectively. In some embodiments, higher doses are effective as well.

III. Combination Therapy of Thyroid Hormone and CHP+Zn

In the following experiments, transgenic animals are treated with CHP+Zn, or T4 plus CHP+Zn between 9 months and 18 months of age. At 14 months and 18 months of age, animals are tested for spatial memory, then sacrificed and tissue analyzed for IDE activity, $A\beta$ 1-40 and 1-42 levels and plaque load. Cognition is measured by Morris Water Maze. IDE activity is measured by radio-ligand assays, soluble and insoluble $A\beta$ is measured by ELISA and western blot, while plaque load is quantitated by thioflavin-S staining, or/and $A\beta$ immunohistochemical analysis.

HuAPP transgenic mice (9 months of age) are divided into 3 groups of 12 animals each (36 animals total) and treated as follows: in the control group, animals are given access to $H_2O$ alone ad libitum; in the CHP+Zn group, animals are given access to 1.0 mg/L CHP+10 mg/L Zn in $H_2O$ ad libitum, in the $T_4$ plus CHP+Zn group, animals are implanted every there months with a thyroid hormone (T4; L-thyroxine) 90 day sustained release pellet (0.1.0 mg/pellet) and are given access to 1.0 mg/L CHP+10 mg/L Zn in $H_2O$ ad libitum.

To determine changes in spatial memory due to CHP+Zn and T4 plus CHP+Zn treatment using the Morris Water Maze. At 14 and 18 months, we test mice in the Morris water maze using a circular pool with movements and data being captured using the SDI SMART video tracking system (San Diego Instruments). Briefly, experiments are run daily for 14 days between 8 a.m. and noon, alternating between control and treated mice. The 7 day acquisition phase consists of four 60 second trials per day with an intertribal interval of 2 minutes. Animals are introduced into the pool facing the wall, alternating between the east and west positions. A trial is stopped when the animal reaches the platform, and is allowed to remain on the platform for 15 seconds. On day 8, learning is evaluated with a single 60-second probe trial in which the platform is removed, and animals are introduced into the maze at the east position. On days 9 and 10, in order to reorient the mice to the north position of the platform, animals repeat four 60 second trials per day as in the acquisition phase. Days 11-13 constitute the reversal phase in which the platform position is changed to the south position in the diagonally opposite quadrant. On day 14, mice are given four 60 second cue trials in which a black and white striped circular platform positioned in the south quadrant is raised 1.5 cm above the water and visibly marked with a flag. Results are averaged across the 4 trials/day and expressed as a daily mean. Dependent variables are latency and distance to reach the platform. Repeated measures analyses of variance (ANOVA) are separately used to analyze the acquisition phase (days 1-7) and the reversal phase (days 11-13), using drug treatment as a between subjects variable and days as within-subjects variable. Post hoc comparisons are by Tukey's multiple comparison test.

To determine changes in IDE activity in huAPP mouse brain due to CHP+Zn and T4 plus CHP+Zn treatment. After spatial testing at 14 months of age (5 months treatment) and 18 months of age (9 months treatment), we sacrifice 6 animals from each group. From these, right brain hemispheres are homogenized and separated into nuclear, soluble and insoluble fractions for protein analysis. Following protein quantification, 0.1 µg of soluble protein is added to 60 µl reaction solution containing 0.1 M phosphate buffer and radiolabeled [125] I-insulin or radiolabeled [125] I $A\beta$ 1-40. Aliquots are taken at indicated times and reactions terminated with 20 µl of 8% SDS sample loading buffer. Samples are boiled and resolved on a 12% polyacrylamide SDS gel, which is then dried. Dried gels are exposed to a Molecular Dynamics phosphor screen with radiolabeled insulin being visualized and quantified on a Molecular Dynamics imager. Insulin degradation is calculated for each group, and statistically analyzed by ANOVA and Newmans-Keuls post hoc test.

To determine changes in $A\beta$ levels in huAPP mouse brain due to CHP+Zn and T4 plus CHP+Zn treatment. Animals are treated, tested and sacrificed as described above.

ELISA: Soluble and insoluble fractions are analyzed for soluble and insoluble forms of $A\beta$ 1-40 and 1-42 by ELISA as described by the manufacturer (Biosource).

Western blot: Soluble and insoluble fractions are boiled for 5 min, spun at 12,000×G for 20 min, and separated (200 µg per lane) by 12.5% SDS-PAGE. Proteins are then transferred to polyvinylidenedifluoride (PVDF) membranes and blocked with 5% (w/v) powdered milk in TBS for two hours. Blocked PDVF membranes are then incubated with primary antibody at 4 OC over night, then washed and incubated with secondary antibody. Detection of bands are by ECL (Pierce) and exposure to XRay film (Kodak). Western blot bands are scanned and imported into ImageJ software for determination of mean grey values with actin staining serving as a normalizing parameter. ELISA data and blot bands are analyzed by ANOVA and Newmans-Keuls post-hoc test.

To determine changes in $A\beta$ plaques in huAPP mouse brain due to CHP+Zn and T4 plus CHP+Zn treatment. We quick freeze the left brain hemispheres of sacrificed mice, section them using a cryostat, thaw mount, and then refreeze them at −80° C. for future use. Thioflavin-S staining: Fixed sections are soaked in 0.25% potassium permanganate solution for 20 min, washed in water, bleached for 2 minutes, washed in water, blocked in 30% H2O2 for 20 min, placed in 0.25% Acetic acid solution for 5 minutes, rinsed in water, then incubated in thioflavin S for 3-5 min. Slides are then mounted using glycerin jelly. 10× digital images are taken on a Zeiss Axioskop 2 plus microscope with fluorescence and processed by Axiovision software. Images are imported into ImageJ software for analysis. Immunohistochemistry: Immediately prior to immunostaining, sections are fixed in 1:1 methanol:acetone for 10 min at −20 OC; treated for 5 min in a 0.5% H2O2 1:1 methanol:PBS solution to inhibit endogenous peroxidase, and then treated with 3% horse serum for 2 hours to block non-specific background. Sections are incubated with the primary antibody 6E10 recognizing Aβ fragment 1-17 (Signet) which has previously been shown to detect plaques in these mice. Bound antibodies are detected using ABC staining kits (Vector). 100-400× digital images are taken on a Zeiss Axioskop 2 plus microscope with fluorescence and processed by Axiovision software. Images are imported into ImageJ software for analysis.

Results. We measure decreased Aβ levels, decreased Aβ plaque load, enhanced IDE activity, and improvement in spatial memory in CHP+Zn treated animals, with synergistic effects in T4 plus CHP+Zn treated animals. Although levels of thyroid hormone used in these experiments are low, there is always a potential that hyperthyroidism induces unwanted side effects in animal models. To minimize these potential effects, mice are observed on a regular basis to note any changes in weight, myxedema, or activity. While there is some data suggesting high levels of Zn is neurotoxic, levels used in these studies are below the recommended daily allowances and should not pose a problem. Nevertheless, animals will be assessed regularly for any signs of lethargy, seizures, increase water intake, or ataxia.

Other data supporting the described results may be found in O'Barr et al., Thyroid Hormone Regulates Endogenous Amyloid-beta Precursor Protein Gene Expression and Processing in Both In Vitro and In Vivo Models, *Thyroid*, 16, 12 (2006), which is hereby incorporated by reference in its entirety.

The various methods and techniques described above provide a number of ways to carry out the invention. Of course, it is to be understood that not necessarily all objectives or advantages described may be achieved in accordance with any particular embodiment described herein.

Furthermore, the skilled artisan will recognize the interchangeability of various features from different embodiments. Similarly, the various features and steps discussed above, as well as other known equivalents for each such feature or step, can be mixed and matched by one of ordinary skill in this art to perform methods in accordance with principles described herein.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

What is claimed is:

1. A method of treating or reducing Alzheimer's disease or dementia in a mammal in need thereof, said method comprising: administering at least once daily to the mammal a pharmaceutical composition comprising a zinc salt and cyclo-Hispro; wherein the weight ratio of zinc to cyclo-Hispro is from about 1:100 to about 100:1.

2. The method of claim 1, wherein the weight ratio of zinc to cyclo-Hispro is from about 1:10 to about 100:1.

3. The method of claim 1, wherein the weight ratio of zinc to cyclo-Hispro is from about 1:6 to about 5:1.

4. The method of claim 1, wherein the weight ratio of zinc to cyclo-Hispro is from about 1:15 to about 20:1.

5. The method of claim 1, wherein the weight ratio of zinc to cyclo-Hispro is from about 1:30 to about 4:1.

6. The method of claim 1, wherein the weight ratio of zinc to cyclo-Hispro is from about 1:8 to about 4:1.

7. The method of claim 1, wherein the weight ratio of zinc to cyclo-Hispro is from about 1:40 to about 40:1.

8. The method of claim 1, further comprising administering a pharmaceutically effective amount of thyroxine to the mammal.

9. A method of treating or reducing Alzheimer's disease or dementia in a mammal in need thereof, said method comprising administering a pharmaceutically effective amount of zinc salt and cyclo-Hispro to the mammal.

10. The method of claim 9, wherein the zinc salt and cyclo-Hispro are administered in an amount that causes an increased serum level of insulin degrading enzyme in the mammal.

11. The method of claim 9, wherein the zinc salt and cyclo-Hispro are administered to the mammal in an amount that causes a decrease in a serum level of amyloid beta protein.

12. The method of claim 9, wherein a zinc cation of the zinc salt is administered to the mammal in an amount from about 0.01 to about 4 mg/kg/day.

13. The method of claim 9, wherein a zinc cation of the zinc salt is administered to the mammal in an amount from about 0.01 to about 1.5 mg/kg/day.

14. The method of claim 9, wherein a zinc cation of the zinc salt is administered to the mammal in an amount from about 0.01 to about 0.4 mg/kg/day.

15. The method of claim 9, wherein a zinc cation of the zinc salt is administered to the mammal in an amount from about 0.1 to about 2 mg/kg/day.

16. The method of claim 9, wherein a zinc cation of the zinc salt is administered to the mammal in an amount from about 2 to about 4 mg/kg/day.

17. The method of claim 9, wherein a zinc cation of the zinc salt is administered to the mammal in an amount from about 1 to about 10 mg/kg/day.

18. The method of claim 9, wherein a zinc cation of the zinc salt is administered to the mammal in an amount from about 3 to about 8 mg/kg/day.

19. The method of claim 9, wherein a zinc cation of the zinc salt is administered to the mammal in an amount from about 4 to about 7 mg/kg/day.

20. The method of claim 9, wherein a zinc cation of the zinc salt is administered to the mammal in an amount from about 7 to about 10 mg/kg/day.

21. The method of claim 9, wherein a zinc cation of the zinc salt is administered to the mammal in an amount from about 0.01 to about 0.1.8 mg/kg/day.

22. The method of claim 9, wherein a zinc cation of the zinc salt is administered to the mammal in an amount from about 1 to about 1.5 mg/kg/day.

23. The method of claim 9, wherein cyclo-Hispro is administered to the mammal in an amount from about 0.007 to about 1.4 mg/kg/day.

24. The method of claim 9, wherein cyclo-Hispro is administered to the mammal in an amount from about 0.01 to about 5 mg/kg/day.

25. The method of claim 9, wherein cyclo-Hispro is administered to the mammal in an amount from about 0.01 to about 2 mg/kg/day.

26. The method of claim 9, wherein cyclo-Hispro is administered to the mammal in an amount from about 2 to about 7 mg/kg/day.

27. The method of claim 9, wherein cyclo-Hispro is administered to the mammal in an amount from about 3 to about 5 mg/kg/day.

28. The method of claim 9, wherein cyclo-Hispro is administered to the mammal in an amount from about 7 to about 10 mg/kg/day.

29. The method of claim 9, wherein cyclo-Hispro is administered to the mammal in an amount from about 0.5 to about 2 mg/kg/day.

30. The method of claim 9, wherein cyclo-Hispro is administered to the mammal in an amount from about 0.2 to about 4 mg/kg/day.

31. The method of claim 9, wherein cyclo-Hispro is administered to the mammal in an amount from about 0.8 to about 3 mg/kg/day.

32. The method of claim 9, wherein cyclo-Hispro is administered to the mammal in an amount from about 1 to about 6 mg/kg/day.

33. A method of treating or reducing Alzheimer's disease or dementia in a mammal in need thereof, said method comprising: administering at least once daily to the mammal a pharmaceutical composition comprising L-thyroxine, a zinc cation and anion, and-cyclo-Hispro; wherein L-thyroxine is administered to the mammal in an amount from about 0.1 to about 15 pg/kg/day; and wherein the zinc cation is administered to the mammal in an amount from about 0.01 to about 10 mg/kg/day; and wherein cyclo-Hispro is administered to the mammal in an amount from about 0.001 to about 10 mg/kg/day.

34. A method of treating or reducing Alzheimer's disease or dementia in a mammal in need thereof, said method comprising administering pharmaceutically effective amount of thyroid hormone, a zinc cation with anion, and cyclo-Hispro to a mammal.

* * * * *